(12) United States Patent
Peake et al.

(10) Patent No.: US 12,354,288 B2
(45) Date of Patent: Jul. 8, 2025

(54) SYSTEM AND METHOD FOR COLLECTION OF FIT DATA RELATED TO A SELECTED MASK

(71) Applicant: ResMed Inc., San Diego, CA (US)

(72) Inventors: Gregory Robert Peake, Sydney (AU); Kristina Mira Zlomislic, Breakfast Point (AU); Rowan Ben Furlong, Sydney (AU)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 18/583,675

(22) Filed: Feb. 21, 2024

(65) Prior Publication Data

US 2024/0257364 A1    Aug. 1, 2024

Related U.S. Application Data

(63) Continuation of application No. 17/421,687, filed as application No. PCT/US2020/060566 on Nov. 13, 2020, now Pat. No. 11,935,252.

(Continued)

(30) Foreign Application Priority Data

Nov. 13, 2019   (AU) .................................. 2019904285

(51) Int. Cl.
*G06T 7/32*       (2017.01)
*A61M 16/06*      (2006.01)
(Continued)

(52) U.S. Cl.
CPC ........... *G06T 7/32* (2017.01); *A61M 16/0605* (2014.02); *G16H 10/20* (2018.01); *G16H 10/60* (2018.01);
(Continued)

(58) Field of Classification Search
None
See application file for complete search history.

(56) References Cited

U.S. PATENT DOCUMENTS 7,866,944 B2   1/2011   Kenyon et al.
8,636,479 B2   1/2014   Kenyon et al.
(Continued)

FOREIGN PATENT DOCUMENTS

CN   104471589 A   3/2015
JP   2008501375 A  1/2008
(Continued)

OTHER PUBLICATIONS

Childers, D.G., et al., The Cepstrum: A Guide to Processing; Proceedings of the IEEE, vol. 65, No. 10, Oct. 1977, 16 pp.

(Continued)

*Primary Examiner* — Leon Flores
(74) *Attorney, Agent, or Firm* — NIXON PEABODY LLP

(57) ABSTRACT

A system and method to collect feedback data from a patient wearing an interface such as a mask when using a respiratory pressure therapy device such as a CPAP device. The system includes a storage device including a facial image of the patient. An interface in communication with the respiratory pressure therapy device collect operational data from when the patient uses the interface. A patient interface collects subjective patient input data from the patient in relation to the patient interface. An analysis module correlates a characteristic of the interface with the facial image data, operational data and subjective patient input data.

20 Claims, 21 Drawing Sheets

Related U.S. Application Data

(60) Provisional application No. 63/072,914, filed on Aug. 31, 2020.

(51) Int. Cl.

| | | |
|---|---|---|
| *G16H 10/20* | (2018.01) | |
| *G16H 10/60* | (2018.01) | |
| *G16H 30/20* | (2018.01) | |
| *G16H 40/60* | (2018.01) | |

(52) U.S. Cl.
CPC ............ *G16H 30/20* (2018.01); *G16H 40/60* (2018.01); *A61M 2205/15* (2013.01); *A61M 2205/35* (2013.01); *A61M 2207/00* (2013.01); *G06T 2207/30201* (2013.01)

(56) References Cited

U.S. PATENT DOCUMENTS

| | | | |
|---|---|---|---|
| 8,638,014 | B2 | 1/2014 | Sears et al. |
| 2012/0245962 | A1 | 9/2012 | Smith et al. |
| 2013/0245462 | A1* | 9/2013 | Capdevila ............ G06T 7/0012 600/479 |
| 2015/0157822 | A1 | 6/2015 | Karpas et al. |
| 2015/0262422 | A1 | 9/2015 | Znamenskiy et al. |
| 2017/0203071 | A1 | 7/2017 | Lawrenson et al. |
| 2019/0184122 | A1 | 6/2019 | Ho et al. |
| 2019/0192799 | A1* | 6/2019 | Steed ................ A61M 16/0622 |
| 2020/0101249 | A1 | 4/2020 | Chodkowski et al. |
| 2020/0384229 | A1* | 12/2020 | Lashinsky .............. G16H 50/50 |

FOREIGN PATENT DOCUMENTS

| | | |
|---|---|---|
| JP | 2013514575 A | 4/2013 |
| JP | 2015524330 A | 8/2015 |
| JP | 2016540603 A | 12/2016 |
| JP | 2017523827 A | 8/2017 |
| WO | 2010091462 A1 | 8/2010 |
| WO | 2013020167 A1 | 2/2013 |
| WO | 2016000040 A1 | 1/2016 |
| WO | 2016172557 A1 | 10/2016 |
| WO | 2017000031 A1 | 1/2017 |
| WO | 2020118311 A1 | 6/2020 |

OTHER PUBLICATIONS

Randall R.B., Frequency Analysis, Copenhagen: Bruel & Kjaer, (1977, revised ed. 1987).

Written Opinion in International Patent Application No. PCT/US2020/060566 mailed Feb. 10, 2020 (6 pp.).

International Search Report in International Patent Application No. PCT/US2020/060566 mailed Feb. 10, 2020 (4 pp.).

* cited by examiner

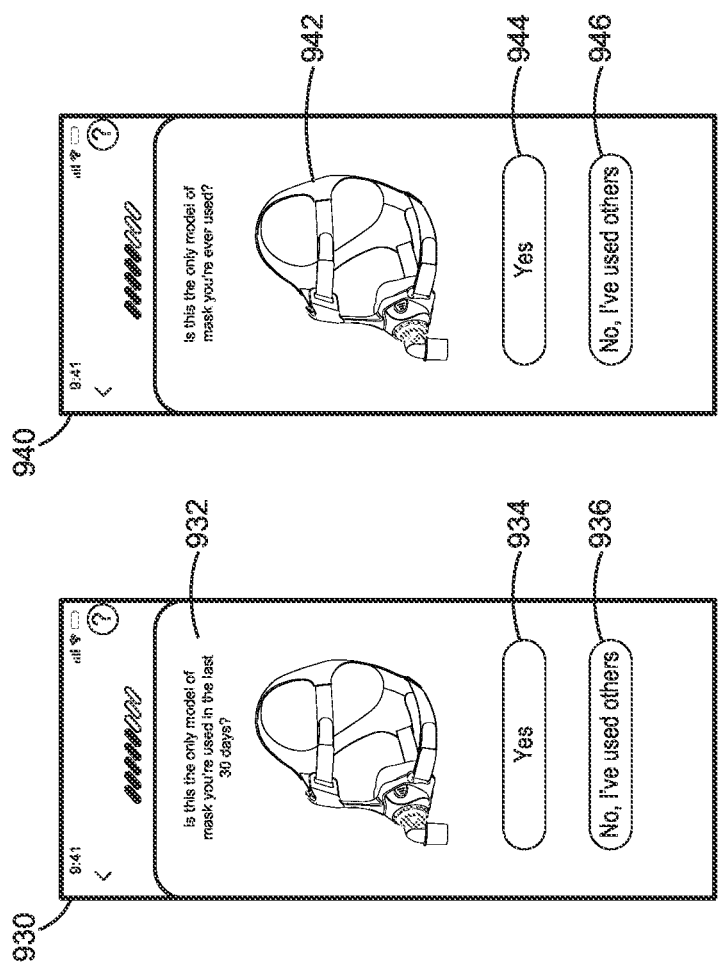

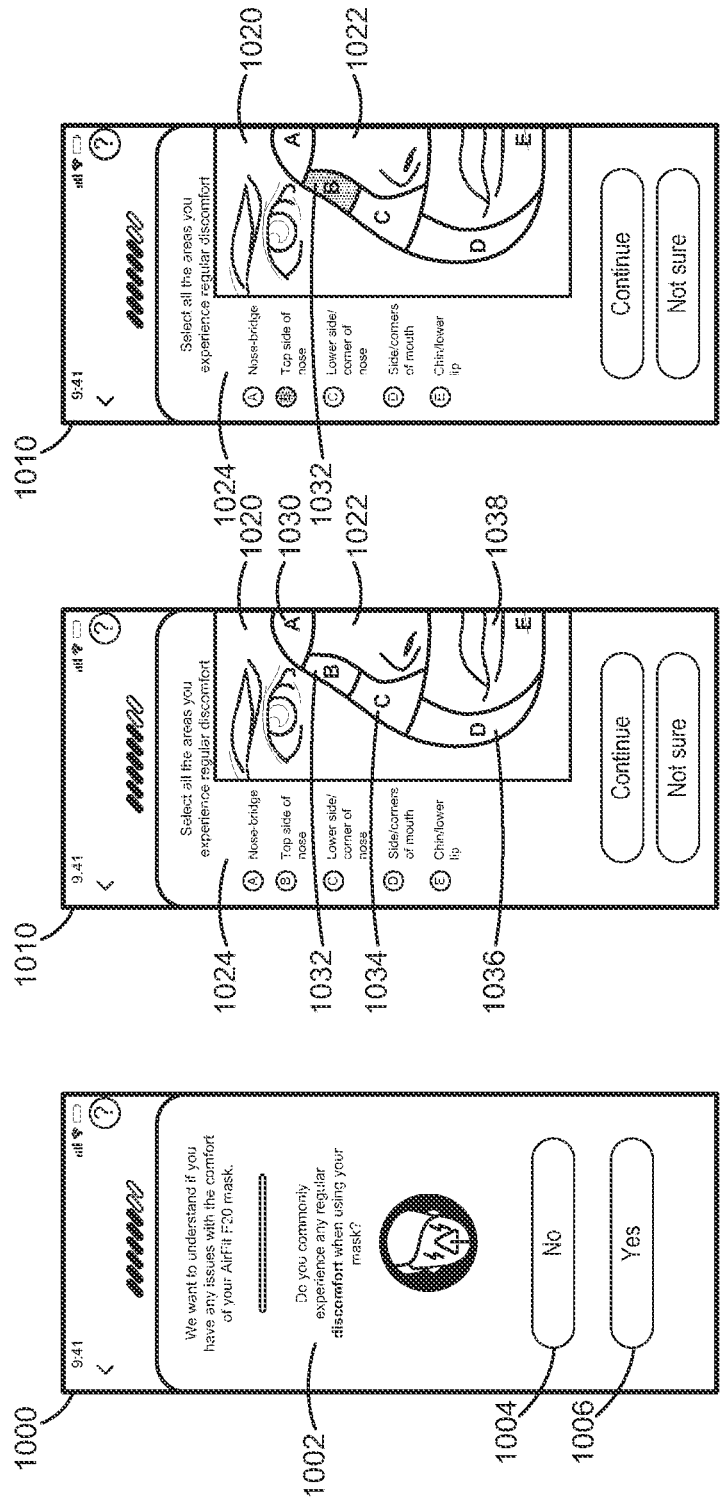

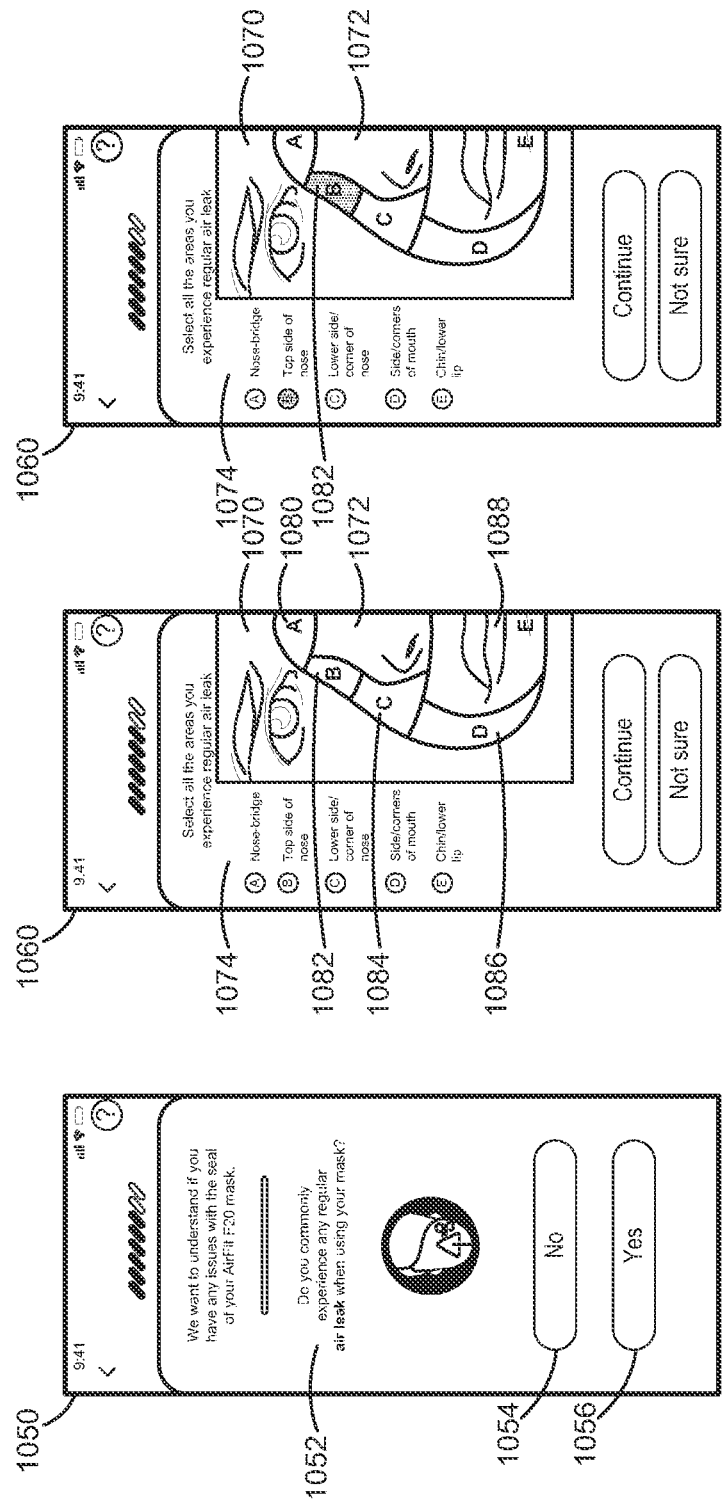

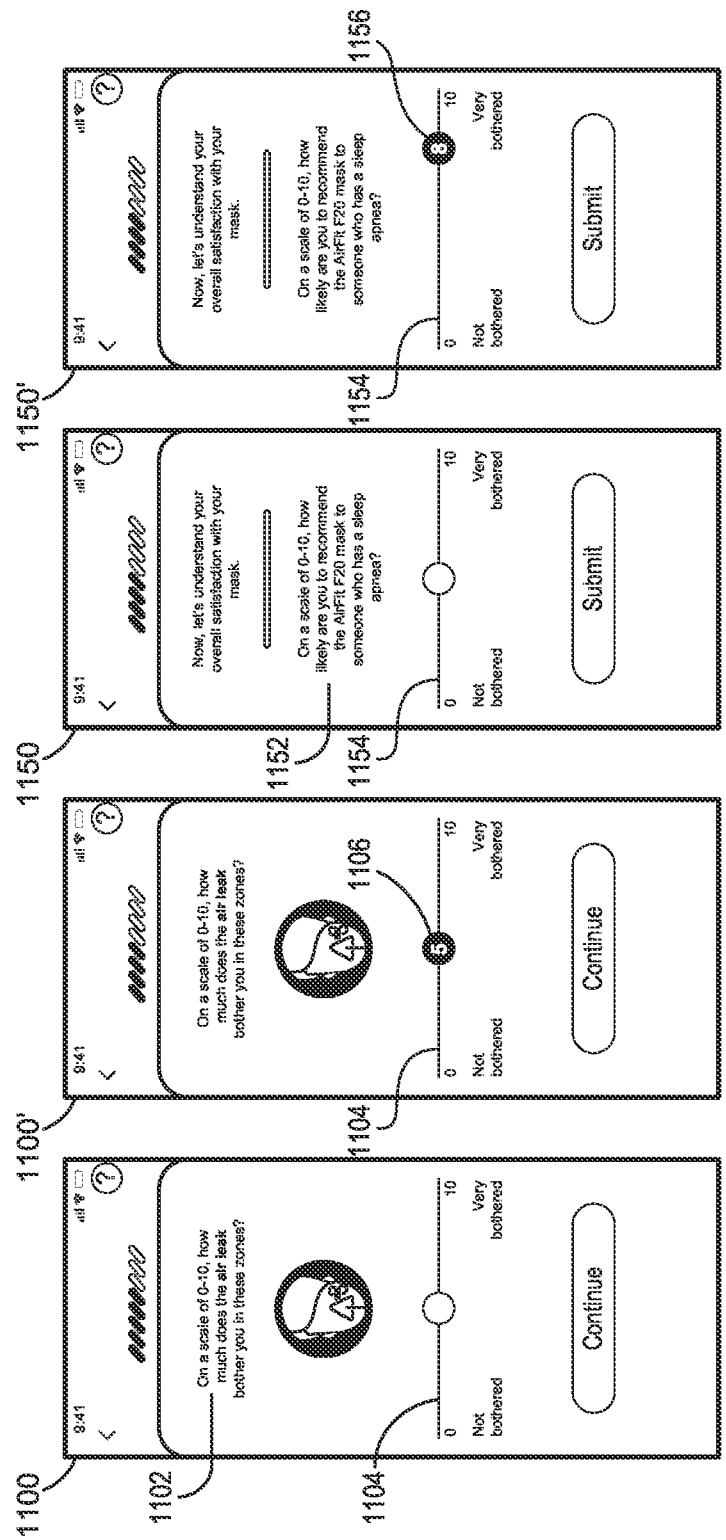

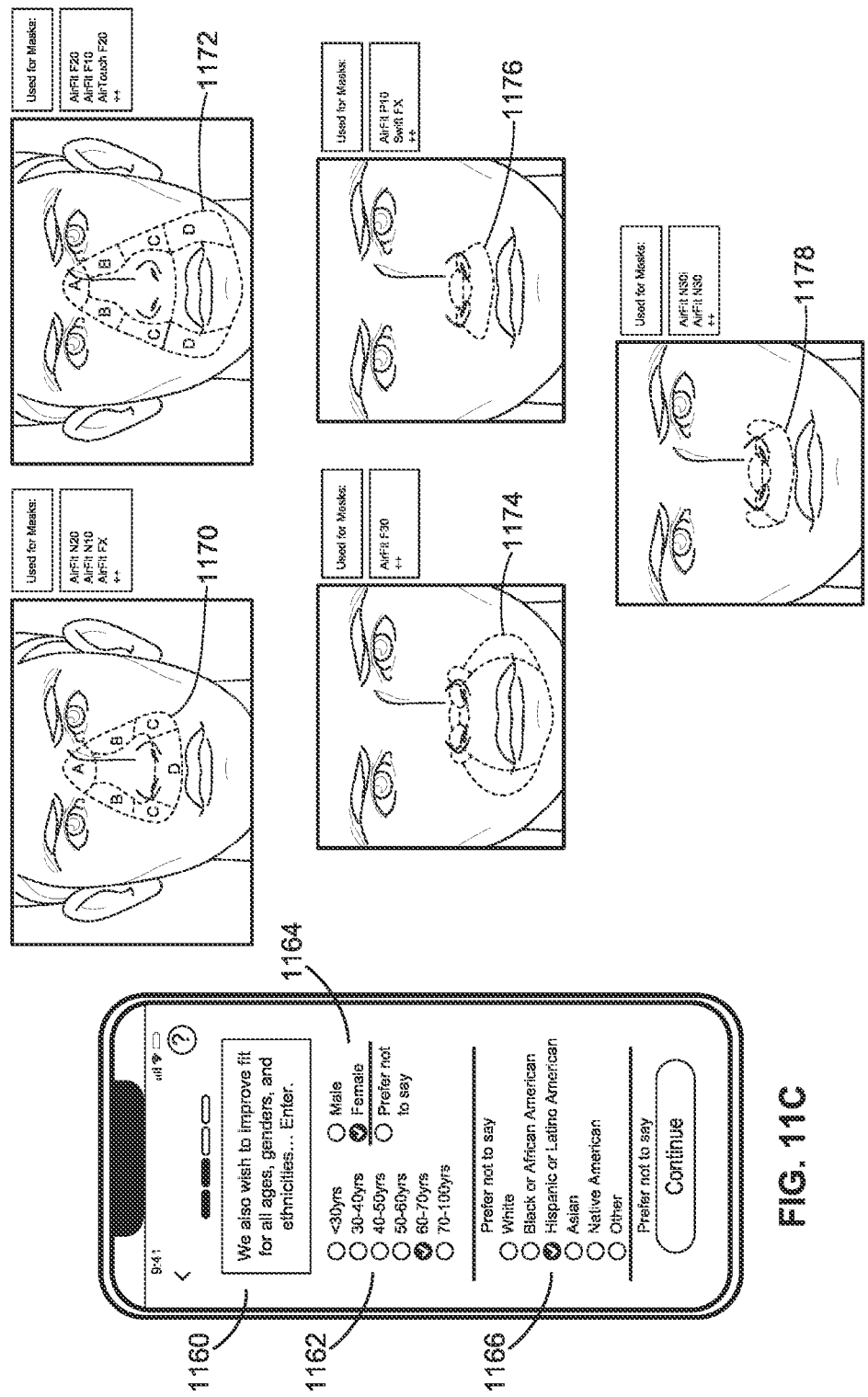

SYSTEM AND METHOD FOR COLLECTION OF FIT DATA RELATED TO A SELECTED MASK

CROSS-REFERENCE TO RELATED APPLICATIONS

This application is a continuation of U.S. patent application Ser. No. 17/421,687 filed Jul. 8, 2021, which has been allowed; U.S. patent application Ser. No. 17/421,687 filed Jul. 8, 2021 is a U.S. National Stage of International Application No. PCT/US2020/060566, filed Nov. 13, 2020, all of which claim priority to and benefit of Australian Provisional Patent Application No. 2019904285, filed Nov. 13, 2019, and U.S. Provisional Patent Application No. 63/072,914 filed Aug. 31, 2020, each of which is incorporated by reference herein in its entirety.

TECHNICAL FIELD

The present disclosure relates generally to designing intake mechanisms for respiratory ailment treatment systems, and more specifically to a system to collect patient data relating to the effectiveness of a mask of an air pressure device for future designers.

BACKGROUND

A range of respiratory disorders exist. Certain disorders may be characterized by particular events, such as apneas, hypopneas, and hyperpneas. Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem.

Other sleep related disorders include Cheyne-Stokes Respiration (CSR), Obesity Hyperventilation Syndrome (OHS) and Chronic Obstructive Pulmonary Disease (COPD). COPD encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors.

Continuous Positive Airway Pressure (CPAP) therapy has been used to treat Obstructive Sleep Apnea (OSA). Application of continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, and Chest Wall disorders. In some forms, the comfort and effectiveness of these therapies may be improved. Invasive ventilation (IV) provides ventilatory support to patients that are no longer able to effectively breathe themselves and may be provided using a tracheostomy tube.

A treatment system may comprise a Respiratory Pressure Therapy (RPT) device, an air circuit, a humidifier, a patient interface, and data management. A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cm H2O relative to ambient pressure. For other forms of therapy, such as the delivery of oxygen, the patient interface may not include a seal sufficient to facilitate delivery to the airways of a supply of gas at a positive pressure of about 10 cm H2O. Treatment of respiratory ailments by such therapy may be voluntary, and hence patients may elect not to comply with therapy if they find devices used to provide such therapy uncomfortable, difficult to use, expensive and/or aesthetically unappealing.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. Obtaining a patient interface allows a patient to engage in positive pressure therapy. Patients seeking their first patient interface or a new patient interface to replace an older interface, typically consult a durable medical equipment provider to determine a recommended patient interface size based on measurements of the patient's facial anatomy, which are typically performed by the durable medical equipment provider. If a mask is uncomfortable or difficult to use, a patient may not comply with therapy. Since it is often recommended that a patient regularly wash their mask, if a mask is difficult to clean (e.g., difficult to assemble or disassemble), patients may not clean their mask and this may impact on patient compliance. In order for the air pressure therapy to effective, not only must comfort be provided to a patient in wearing the mask, but a solid seal must be created between the face and the mask to minimize air leaks.

Patient interfaces, as described above, may be provided to a patient in various forms, such as a nasal mask or full-face mask/oro-nasal mask (FFM) or nasal pillows mask, for example. Such patient interfaces are manufactured with various dimensions to accommodate a specific patient's anatomical features in order to facilitate a comfortable interface that is functional to provide, for example, positive pressure therapy. Such patient interface dimensions may be customized to correspond with a particular patient's specific facial anatomy or may be designed to accommodate a population of individuals that have an anatomy that falls within predefined spatial boundaries or ranges. However, in some cases masks may come in a variety of standard sizes from which a suitable one must be chosen.

In this regard, sizing a patient interface for a patient is typically performed by a trained individual, such as a Durable Medical Equipment (DME) provider or a physician. Typically, a patient needing a patient interface to begin or continue positive pressure therapy visits the trained individual at an accommodating facility where a series of measurements are made in an effort to determine an appropriate patient interface size from standard sizes. An appropriate size is intended to mean a particular combination of dimensions of certain features, such as the seal forming structure, of a patient interface, which provide adequate comfort and sealing to effectuate positive pressure therapy. Sizing in this way is not only labor intensive but also inconvenient. The inconvenience of taking time out of a busy schedule or, in some instances, having to travel great distances is a barrier to many patients receiving a new or replacement patient interface and ultimately a barrier to receiving treatment. This inconvenience prevents patients from receiving a needed patient interface and from engaging in positive pressure therapy. Nevertheless, selection of the most appropriate size is important for treatment quality and compliance.

There is a need for future mask designers to obtain feedback from mask users to better design interfaces. There is a need for a system that collects mask user feedback data in relation to stored facial dimension data for a wide population of users. There is a need for a system that correlates user feedback data with other data related to a selected mask.

SUMMARY

The disclosed system provides an adaptable system to collect user feedback data relating to masks for use with an RPT device. The system combines facial image data with collected RPT operational data and other data such as subjective data from a population of patients to assist in the design of masks.

One disclosed example is a method of collecting data relating to a patient interface for a respiratory pressure therapy device. Facial image data from the patient is correlated with the patient. Operational data of the respiratory therapy device used by the patient with the patient interface is collected. Subjective patient input data is collected from the patient in relation to the patient interface. A characteristic of the interface is correlated with the facial image data, operational data and subjective patient input data.

In other implementations of the above disclosed method, the patient interface is a mask. In another implementation, the respiratory pressure therapy device is one of a Continuous Positive Airway Pressure (CPAP) device, a Non-invasive ventilation (NIV) device, or an invasive ventilation device. In another implementation, the facial image data is taken from a mobile device with an application to capture the facial image of the patient. In another implementation, the method further includes displaying a facial image with an interposed image of the interface and collecting subjective data from the patient based on a location on the interposed image of the interface. In another implementation, the subjective data is collected by displaying a question in an interface on a mobile device. In another implementation, the interface displays a sliding scale to input the answer of the patient. In another implementation, the facial image data include face height, nose width, and nose depth. In another implementation, the method includes adjusting the characteristic of the interface to prevent leaks. The characteristic is associated with contact between a facial surface and the interface. In another implementation, the method includes adjusting the characteristic of the interface to increase comfort. The characteristic is associated with contact between a facial surface. In another implementation, facial image data from a second patient similar to the patient, operational data of a respiratory therapy device used by the second patient, and subjective data input from the second patient is collected and used in correlating the characteristic of the interface. In another implementation, facial image data, operational data and subjective patient input data from multiple patients including the patient is collected. Machine learning is applied to determine types of operational data, subjective data, and facial image data correlated with the characteristic to adjust the characteristic of the interface.

Another disclosed example is a system having a control system including one or more processors and a memory storing machine readable instructions. The control system is coupled to the memory. The above described methods are implemented when the machine executable instructions in the memory are executed by one of the processors of the control system.

Another disclosed example is a system for communicating one or more indications to a user. The system includes a control system configured to implement one of the above described methods.

Another disclosed example is a computer program product having instructions which, when executed by a computer, cause the computer to carry out one of the above described methods. Another implementation of the example computer program product is where the computer program product is a non-transitory computer readable medium.

Another disclosed example is a system to collect feedback data from a patient using an interface with a respiratory pressure therapy device. The system includes a storage device storing a facial image of the patient. A data communication interface is in communication with the respiratory pressure therapy device to collect operational data from when the patient uses the interface. A patient data collection interface collects subjective patient input data from the patient in relation to the patient interface. An analysis module is operable to correlate a characteristic of the interface with the facial image data, operational data and subjective patient input data In other implementations of the above disclosed system, the system includes a manufacturing system producing the interface based on design data. The analysis module adjusts the design data based on the correlated characteristic. In another implementation, the patient interface is a mask. In another implementation, the respiratory pressure therapy device is one of a Continuous Positive Airway Pressure (CPAP) device, a Non-invasive ventilation (NIV) device, or an invasive ventilation device. In another implementation of the system, a mobile device executes an application to capture the facial image of the patient. In another implementation, the patient data collection interface displays a facial image with an interposed image of the interface and collects subjective data from the patient based on location on the interposed image of the interface. In another implementation, the subjective data is collected by displaying questions in an interface on a mobile device. In another implementation, the interface displays a sliding scale to input the answer of the patient. In another implementation, the facial image data include face height, nose width, and nose depth. In another implementation, the characteristic of the interface is adjusted to prevent leaks. The characteristic is associated with contact between a facial surface and the interface. In another implementation, the characteristic of the interface is adjusted to increase comfort. The characteristic is associated with contact between a facial surface and the interface. In another implementation, the system includes a machine learning module operable to determine operational data, subjective data, and facial image data from multiple patients correlated with the characteristic to adjust the characteristic of the interface.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The disclosure will be better understood from the following description of exemplary embodiments together with reference to the accompanying drawings, in which:

FIG. 9D is an example interface that determines the short term use of a mask;

FIG. 9E is an example interface that determines the long term use of a mask;

FIG. 10A is an example interface that provides instructions to determine the location of mask discomfort;

FIG. 10B is an example interface that allows a user to select graphically where mask discomfort occurs;

FIG. 10C is the example interface in FIG. 10B after a user selects an area of discomfort;

FIG. 10D is an example interface that provides instructions to determine the location of mask air leaks;

FIG. 10E is an example interface that allows a user to select graphically where mask air leaks occur;

FIG. 10F is the example interface in FIG. 10B after a user selects an area where a mask leak has occurred;

FIG. 11A is an example slider interface to collect subjective data on the impact of an air leak;

FIG. 11B is an example slider interface to collect subjective data on the patient satisfaction with a mask;

FIG. 11C is an example interface to collect patient demographic data;

FIG. 11D are example graphics that may be interposed for collecting discomfort and air leaks depending on the selected mask type;

Figure 1:
FIG. 1 shows a system including a patient wearing a patient interface in the form of a full-face mask to receive PAP therapy from an example respiratory pressure therapy device.

The present disclosure is susceptible to various modifications and alternative forms. Some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

The present inventions can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

The present disclosure relates to a system and method for collecting feedback data from masks selected for users of respiratory pressure therapy devices. Masks are sized based on facial data collected for a user. The users are presented an interface that collects feedback data on the sized masks. The data is analyzed in order to further refine designs of masks for similar patients based on factors such as operational data, patient demographics, patient facial features and the like.

FIG. 1 shows a system including a patient 10 wearing a patient interface 100, in the form of a full-face mask (FFM), receiving a supply of air at positive pressure from a respiratory pressure therapy (RPT) device 40. Air from the RPT device 40 is humidified in a humidifier 60, and passes along an air circuit 50 to the patient 10.

Figure 2:
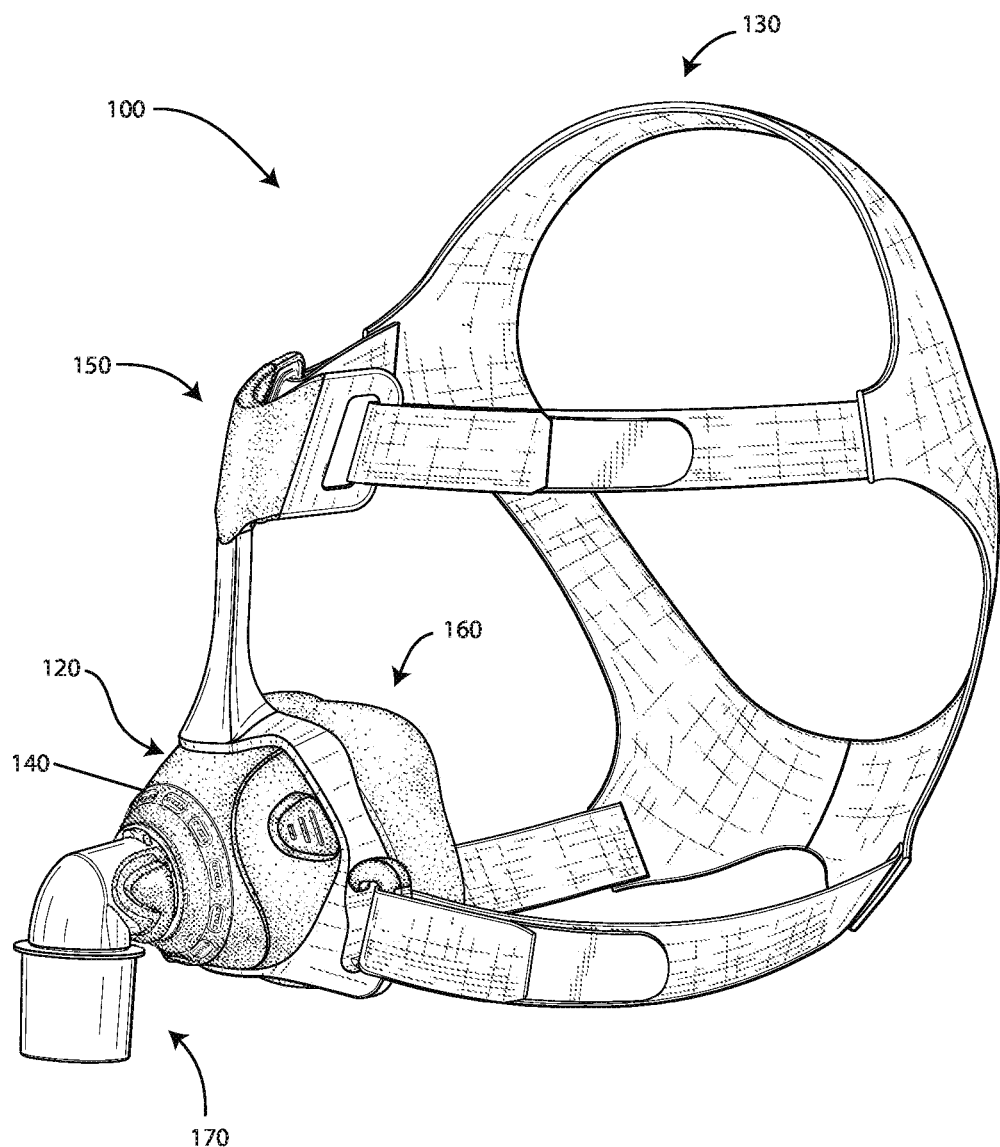
FIG. 2 shows a patient interface in the form of a nasal mask with headgear in accordance with one form of the present technology.

FIG. 2 depicts the patient interface 100 in accordance with one aspect of the present technology that comprises the following functional aspects: a seal-forming structure 160, a plenum chamber 120, a positioning and stabilising structure 130, a vent 140, a forehead support 150, one form of connection port 170 for connection to the air circuit 50 in FIG. 1. In some forms a functional aspect may be provided by one or more physical components. In some forms, one physical component may provide one or more functional aspects. In use the seal-forming structure 160 is arranged to surround an entrance to the airways of the patient so as to facilitate the supply of air at positive pressure to the airways.

In one form of the present technology, a seal-forming structure 160 provides a seal-forming surface, and may additionally provide a cushioning function. The seal-forming structure 160 in accordance with the present technology may be constructed from a soft, flexible, resilient material such as silicone. In one form the seal-forming portion of the non-invasive patient interface 100 comprises a pair of nasal puffs, or nasal pillows, each nasal puff or nasal pillow being constructed and arranged to form a seal with a respective naris of the nose of a patient.

Nasal pillows in accordance the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 100 comprises a seal-forming portion that forms a seal in use on an upper lip region (that is, the lip superior) of the patient's face. In one form the non-invasive patient interface 100 comprises a seal-forming portion that forms a seal in use on a chin-region of the patient's face.

Preferably the plenum chamber 120 has a perimeter that is shaped to be complementary to the surface contour of the face of an average person in the region where a seal will form in use. In use, a marginal edge of the plenum chamber 120 is positioned in close proximity to an adjacent surface of the face. Actual contact with the face is provided by the seal-forming structure 160. The seal-forming structure 160 may extend in use about the entire perimeter of the plenum chamber 120.

Preferably the seal-forming structure 160 of the patient interface 100 of the present technology may be held in sealing position in use by the positioning and stabilising structure 130.

In one form, the patient interface 100 includes a vent 140 constructed and arranged to allow for the washout of exhaled carbon dioxide. One form of vent 140 in accordance with the present technology comprises a plurality of holes, for example, about 20 to about 80 holes, or about 40 to about 60 holes, or about 45 to about 55 holes.

Figure 3A:
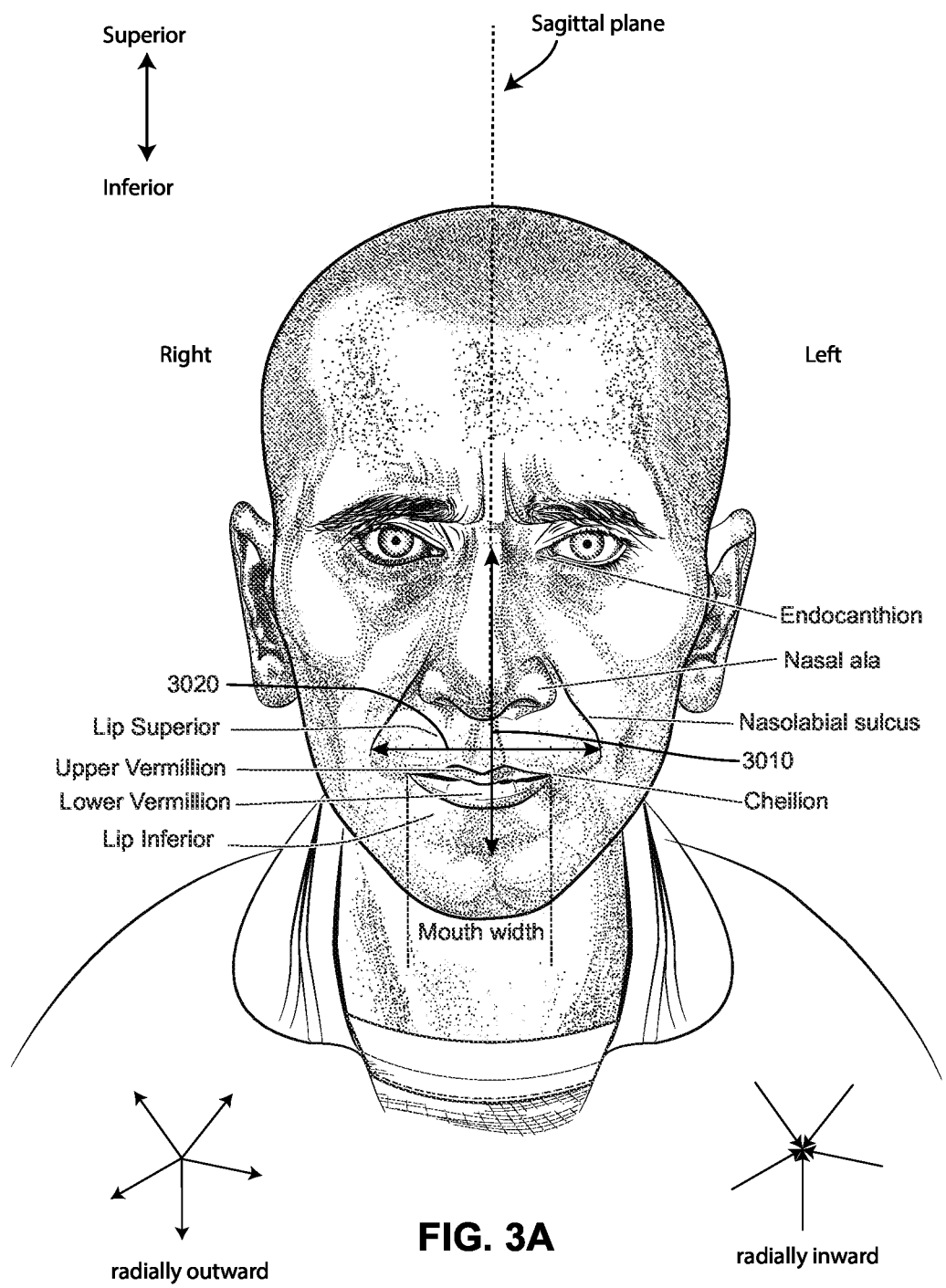
FIG. 3A is a front view of a face with several features of surface anatomy.
Figure 3B:
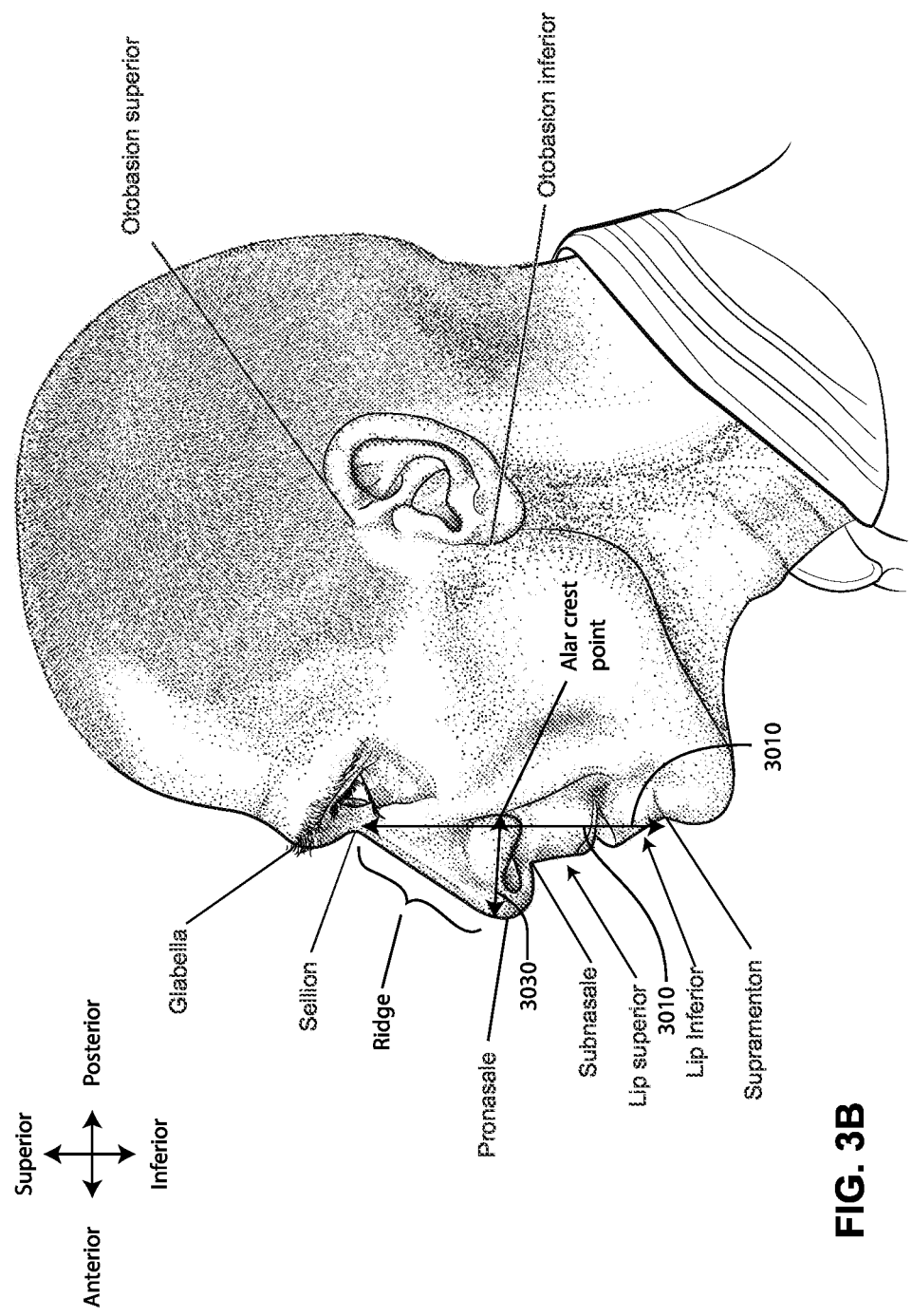
FIG. 3B is a side view of a head with several features of surface anatomy identified.
Figure 3C:
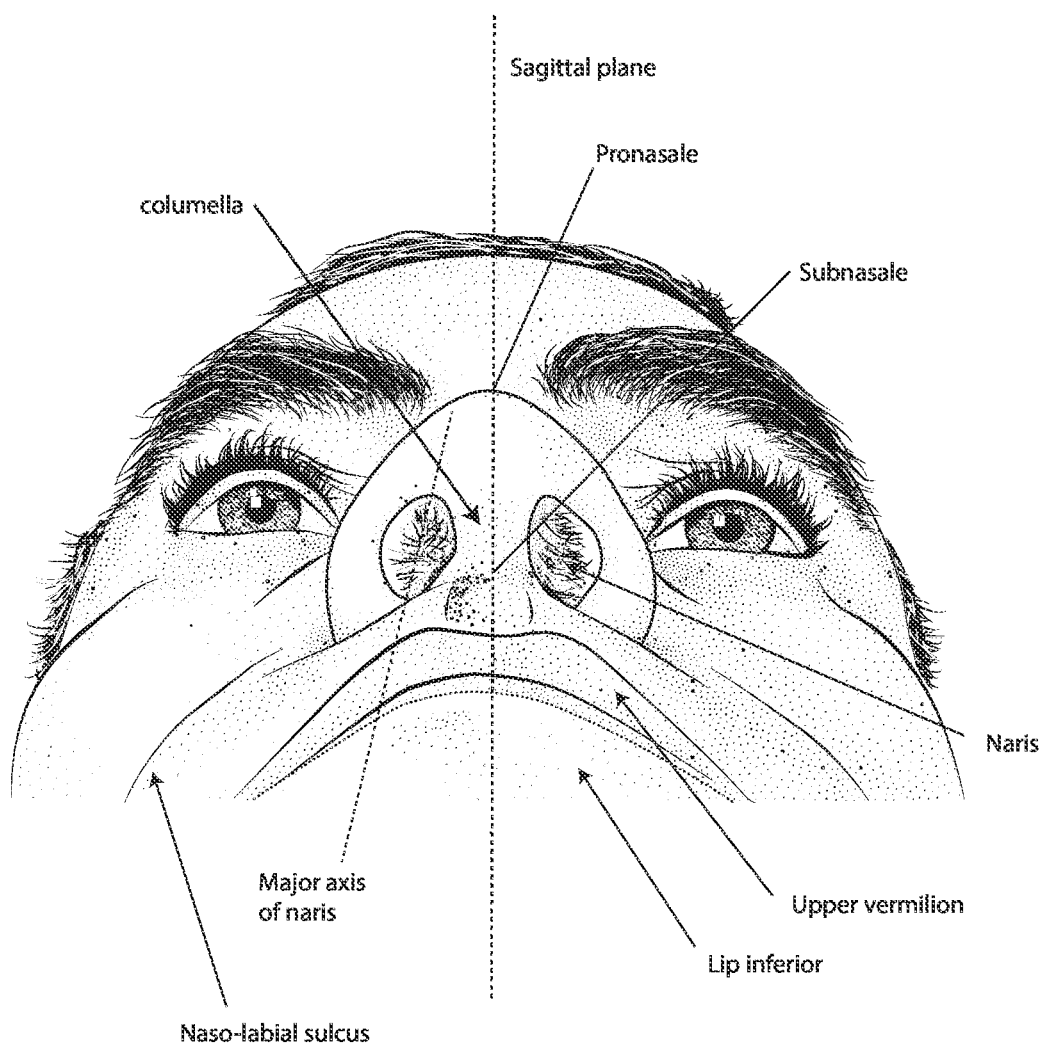
FIG. 3C is a base view of a nose with several features identified.

FIG. 3A shows an anterior view of a human face including the endocanthion, nasal ala, nasolabial sulcus, lip superior and inferior, upper and lower vermillion, and chelion. Also shown are the mouth width, the sagittal plane dividing the head into left and right portions, and directional indicators. The directional indicators indicate radial inward/outward and superior/inferior directions. FIG. 3B shows a lateral view of a human face including the glabaella, sellion, nasal ridge, pronasale, subnasale, superior and inferior lip, supramenton, alar crest point, and otobasion superior and inferior. Also shown are directional indictors indicating superior/inferior and anterior/posterior directions. FIG. 3C shows a base view of a nose with several features identified including naso-labial sulcus, lip inferior, upper Vermilion, naris, subnasale, columella, pronasale, the major axis of a naris and the sagittal plane.

The following are more detailed explanations of the features of the human face shown in FIGS. 3A-3C.

Ala: The external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

Columella: The strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Glabella: Located on the soft tissue, the most prominent point in the midsagittal plane of the forehead.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: The most protruded point or tip of the nose, which can be identified in lateral view of the rest of the portion of the head.

Philtrum: The midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion.

As will be explained below, there are several critical dimensions from a face that may be used to select the sizing for a patient interface such as the mask 100 in FIG. 1. In this example there are three dimensions including the face height, the nose width, and the nose depth. FIGS. 3A-3B show a line 3010 that represents the face height. As may be seen in FIG. 3B, the face height is the distance between the sellion to the supramenton. A line 3020 in FIG. 3A represents the nose width, which is between the left and right alar points of the nose. A line 3030 in FIG. 3B represents the nose depth.

Figure 4A:
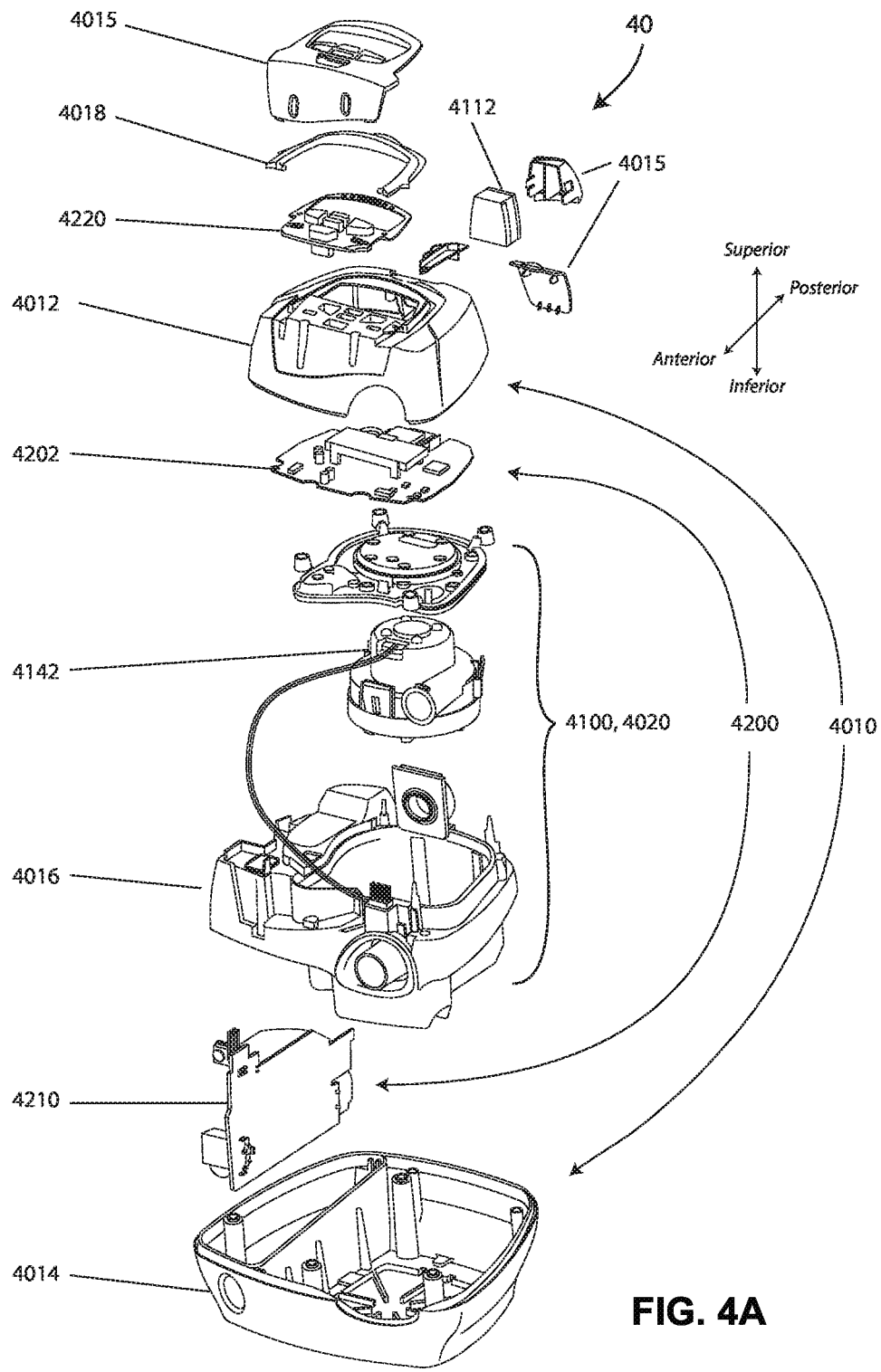
FIG. 4A shows a respiratory pressure therapy device in accordance with one form of the present technology.
Figure 4B:
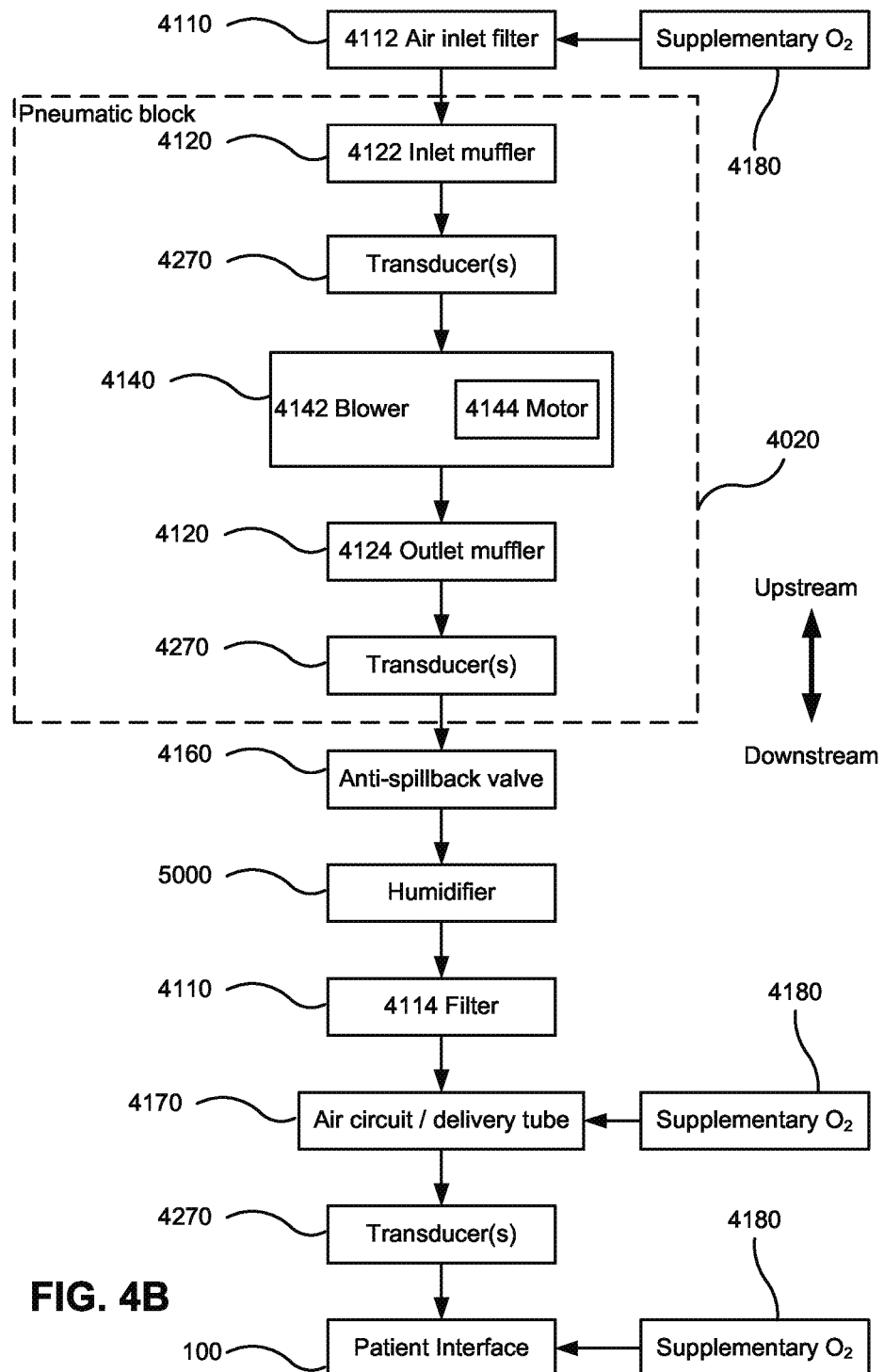
FIG. 4B is a schematic diagram of the pneumatic path of a respiratory pressure therapy device in accordance with one form of the present technology.
Figure 4C:
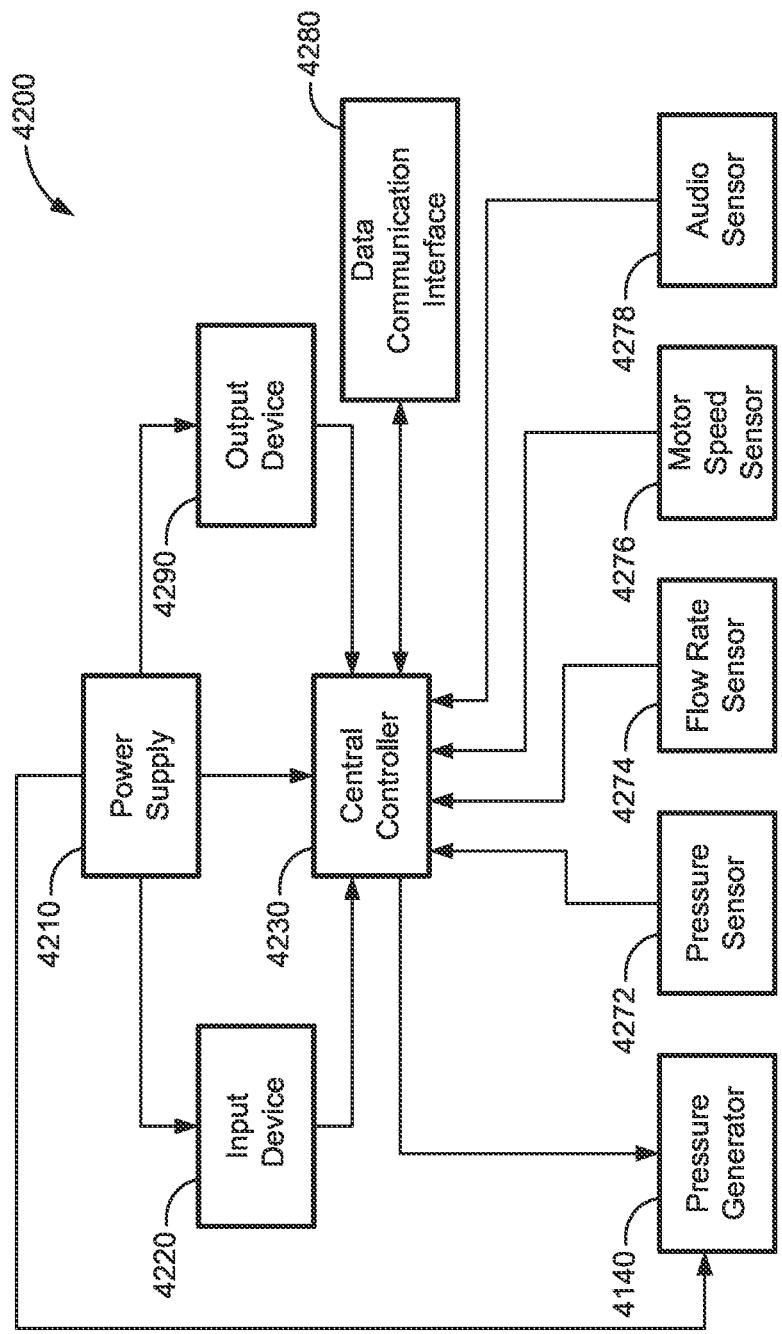
FIG. 4C is a schematic diagram of the electrical components of a respiratory pressure therapy device in accordance with one form of the present technology.

FIG. 4A shows an exploded view of the components of an example RPT device 40 in accordance with one aspect of the present technology comprises mechanical, pneumatic, and/or electrical components and is configured to execute one or more algorithms, such as any of the methods, in whole or in part, described herein. FIG. 4B shows a block diagram of the example RPT device 40. FIG. 4C shows a block diagram of the electrical control components of the example RPT device 40. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface. The RPT device 40 may be configured to generate a flow of air for delivery to a patient's airways, such as to treat one or more of the respiratory conditions.

The RPT device 40 may have an external housing 4010, formed in two parts, an upper portion 4012 and a lower portion 4014. Furthermore, the external housing 4010 may include one or more panel(s) 4015. The RPT device 40 comprises a chassis 4016 that supports one or more internal components of the RPT device 40. The RPT device 40 may include a handle 4018.

The pneumatic path of the RPT device 40 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as a pressure sensor 4272, a flow rate sensor 4274, and a motor speed sensor 4276.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 40 may have an electrical power supply 4210, one or more input devices 4220, a central controller 4230, a pressure generator 4140, a data communication interface 4280, and one or more output devices 4290. A separate controller may be provided for the therapy device. Electrical components 4200 may be mounted on a single Printed Circuit Board Assembly (PCBA) 4202. In an alternative form, the RPT device 40 may include more than one PCBA 4202. Other components such as the one or more protection circuits 4250, transducers 4270, the data communication interface 4280, and storage devices may also be mounted on the PCBA 4202.

An RPT device may comprise one or more of the following components in an integral unit. In an alternative form, one or more of the following components may be located as respective separate units.

An RPT device in accordance with one form of the present technology may include an air filter 4110, or a plurality of air filters 4110. In one form, an inlet air filter 4112 is located at the beginning of the pneumatic path upstream of a pressure generator 4140. In one form, an outlet air filter 4114, for example an antibacterial filter, is located between an outlet of the pneumatic block 4020 and a patient interface 100.

An RPT device in accordance with one form of the present technology may include a muffler 4120, or a plurality of mufflers 4120. In one form of the present technology, an inlet muffler 4122 is located in the pneumatic path upstream of a pressure generator 4140. In one form of the present technology, an outlet muffler 4124 is located in the pneumatic path between the pressure generator 4140 and a patient interface 100 in FIG. 1.

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cm H2O to about 20 cm H2O, or in other forms up to about 30 cm H2O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240. In other forms, a pressure generator 4140 may be a piston-driven pump, a pressure regulator connected to a high pressure source (e.g. compressed air reservoir), or a bellows.

An air circuit 4170 in accordance with an aspect of the present technology is a conduit or a tube constructed and arranged to allow, in use, a pressurized flow of air to travel between two components such as the humidifier 60 and the patient interface 100. In particular, the air circuit 4170 may be in fluid communication with the outlet of the humidifier 60 and the plenum chamber 120 of the patient interface 100.

In one form of the present technology, an anti-spill back valve 4160 is located between the humidifier 60 and the pneumatic block 4020. The anti-spill back valve is constructed and arranged to reduce the risk that water will flow upstream from the humidifier 60, for example to the motor 4144.

A power supply 4210 may be located internal or external of the external housing 4010 of the RPT device 40. In one form of the present technology, power supply 4210 provides electrical power to the RPT device 40 only. In another form of the present technology, power supply 4210 provides electrical power to both RPT device 40 and humidifier 60.

An RT system may comprise one or more transducers (sensors) 4270 configured to measure one or more of any number of parameters in relation to an RT system, its patient, and/or its environment. A transducer may be configured to produce an output signal representative of the one or more parameters that the transducer is configured to measure.

The output signal may be one or more of an electrical signal, a magnetic signal, a mechanical signal, a visual signal, an optical signal, a sound signal, or any number of others which are known in the art.

A transducer may be integrated with another component of an RT system, where one exemplary arrangement would be the transducer being internal of an RPT device. A transducer may be substantially a 'standalone' component of an RT system, an exemplary arrangement of which would be the transducer being external to the RPT device.

A transducer may be configured to communicate its output signal to one or more components of an RT system, such as an RPT device, a local external device, or a remote external device. External transducers may be for example located on a patient interface, or in an external computing device, such as a smartphone. External transducers may be located for example on or form part of the air circuit, e.g., the patient interface.

The one or more transducers 4270 may be constructed and arranged to generate signals representing properties of air such as a flow rate, a pressure or a temperature. The air may be a flow of air from the RPT device to a patient, a flow of air from the patient to the atmosphere, ambient air or any others. The signals may be representative of properties of the flow of air at a particular point, such as the flow of air in the pneumatic path between the RPT device and the patient. In one form of the present technology, one or more transducers 4270 are located in a pneumatic path of the RPT device, such as downstream of the humidifier 60.

In accordance with one aspect of the present technology, the one or more transducers 4270 comprises a pressure sensor located in fluid communication with the pneumatic path. An example of a suitable pressure sensor is a transducer from the HONEYWELL ASDX series. An alternative suitable pressure sensor is a transducer from the NPA Series from GENERAL ELECTRIC. In one implementation, the pressure sensor is located in the air circuit 4170 adjacent the outlet of the humidifier 60.

A microphone pressure sensor 4278 is configured to generate a sound signal representing the variation of pressure within the air circuit 4170. The sound signal from the microphone 4278 may be received by the central controller 4230 for acoustic processing and analysis as configured by one or more of the algorithms described below. The microphone 4278 may be directly exposed to the airpath for greater sensitivity to sound, or may be encapsulated behind a thin layer of flexible membrane material. This membrane may function to protect the microphone 4278 from heat and/or humidity.

Data from the transducers 4270 such as the pressure sensor 4272, flow rate sensor 4274, motor speed sensor 4276, and microphone 4278 may be collected by central controller 4230 on a periodic basis. Such data generally relates to the operational state of the RPT device 40. In this example, the central controller 4230 encodes such data from the sensors in a proprietary data format. The data may also be coded in a standardized data format.

In one form of the present technology, an RPT device 40 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230. In one form, the input device 4220 may be constructed and arranged to allow a person to select a value and/or a menu option.

In one form of the present technology, the central controller 4230 is one or a plurality of processors suitable to control an RPT device 40. Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable. In one form of the present technology, the central controller 4230 is a dedicated electronic circuit. In one form, the central controller 4230 is an application-specific integrated circuit. In another form, the central controller 4230 comprises discrete electronic components. The central controller 4230 may be configured to receive input signal(s) from one or more transducers 4270, one or more input devices 4220, and the humidifier 60.

The central controller 4230 may be configured to provide output signal(s) to one or more of an output device 4290, a therapy device controller 4240, a data communication interface 4280, and the humidifier 60.

In some forms of the present technology, the central controller 4230 is configured to implement the one or more methodologies described herein, such as the one or more algorithms expressed as computer programs stored in a non-transitory computer readable storage medium, on an internal memory. In some forms of the present technology, the central controller 4230 may be integrated with an RPT device 40. However, in some forms of the present technology, some methodologies may be performed by a remotely located device such as a mobile computing device. For example, the remotely located device may determine control settings for a ventilator or detect respiratory related events by analysis of stored data such as from any of the sensors described herein. As explained above, all data and operations for external sources or the central controller 4230 are generally proprietary to the manufacturer of the RPT device 40. Thus, the data from the sensors and any other additional operational data is not generally accessible by any other device.

In one form of the present technology, a data communication interface is provided, and is connected to the central controller 4230. The data communication interface may be connectable to a remote external communication network and/or a local external communication network. The remote external communication network may be connectable to remote external devices such as servers or databases. The local external communication network may be connectable to a local external device such as a mobile device or a health monitoring device. Thus, the local external communication network may be used by either the RPT device 40 or a mobile device to collect data from other devices.

In one form, the data communication interface is part of the central controller 4230. In another form, data communication interface 4280 is separate from the central controller 4230, and may comprise an integrated circuit or a processor. In one form, the remote external communication network is the Internet. The data communication interface may use wired communication (e.g. via Ethernet, or optical fiber) or a wireless protocol (e.g. CDMA, GSM, 2G, 3G, 4G/LTE, LTE Cat-M, NB-IoT, 5G New Radio, satellite, beyond 5G) to connect to the Internet. In one form, local external communication network 4284 utilizes one or more communication standards, such as Bluetooth, or a consumer infrared protocol.

The example RPT device 40 includes integrated sensors and communication electronics as shown in FIG. 4C. Older RPT devices may be retrofitted with a sensor module that may include communication electronics for transmitting collected data. Such a sensor module could be attached to the RPT device and thus transmit operational data to a remote analysis engine.

Some implementations of the disclosed acoustic analysis technologies may implement cepstrum analysis based on audio signals from a sensor such as the audio sensor 4278. Audio signals may reflect user physiological states such as sleeping or breathing as well as operational data of the RPT. A cepstrum may be considered the inverse Fourier Transform of the log spectrum of the forward Fourier Transform of the decibel spectrum, etc. The operation essentially can convert a convolution of an impulse response function (IRF) and a sound source into an addition operation so that the sound source may then be more easily accounted for or removed so as to isolate data of the IRF for analysis. Techniques of cepstrum analysis are described in detail in a scientific paper entitled "The Cepstrum: A Guide to Processing" (Childers et al, Proceedings of the IEEE, Vol. 65, No. 10, October 1977) and Randall R B, Frequency Analysis, Copenhagen: Bruel & Kjaer, p. 344 (1977, revised ed. 1987). The application of cepstrum analysis to respiratory therapy system component identification is described in detail in PCT Publication No. WO2010/091462, titled "Acoustic Detection for Respiratory Treatment Apparatus," the entire contents of which are hereby incorporated by reference.

As previously mentioned, a respiratory therapy system typically includes an RPT device, a humidifier, an air delivery conduit, and a patient interface such as those components shown in FIG. 1. A variety of different forms of patient interfaces may be used with a given RPT device, for example nasal pillows, nasal prongs, nasal masks, nose & mouth (oronasal) masks, or full face masks. Furthermore, different forms of air delivery conduit may be used. In order to provide improved control of therapy delivered to the patient interface, measuring or estimating treatment parameters such as pressure in the patient interface, and vent flow may be analyzed. In older systems knowledge of the type of component being used by a patient can be determined as will be explained below to determine optimal interfaces for a patient. Some RPT devices include a menu system that allows the patient to select the type of system components, including the patient interface, being used, e.g., brand, form, model, etc. Once the types of the components are entered by the patient, the RPT device can select appropriate operating parameters of the flow generator that best coordinate with the selected components. The data collected by the RPT device may be used to evaluate the effectiveness of the particular selected components such as a patient interface in supplying pressurized air to the patient.

This technology includes an analysis method that enables the separation of the acoustic mask reflections from the other system noises and responses, including but not limited to blower sound. This makes it possible to identify differences between acoustic reflections (usually dictated by mask shapes, configurations and materials) from different masks and may permit the identification of different masks without user or patient intervention.

An example method of identifying the mask is to sample the output sound signal y(t) generated by the microphone 4278 at at least the Nyquist rate, for example 20 kHz, compute the cepstrum from the sampled output signal, and then separate a reflection component of the cepstrum from the input signal component of the cepstrum. The reflection component of the cepstrum comprises the acoustic reflection from the mask of the input sound signal, and is therefore referred to as the "acoustic signature" of the mask, or the "mask signature." The acoustic signature is then compared with a predefined or predetermined database of previously measured acoustic signatures obtained from systems containing known masks. Optionally, some criteria would be set to determine appropriate similarity. In one example embodiment, the comparisons may be completed based on the single largest data peak in the cross-correlation between the measured and stored acoustic signatures. However, this approach may be improved by comparisons over several data peaks or alternatively, wherein the comparisons are completed on extracted unique sets of cepstrum features.

In accordance with the present technology, data associated with the reflection component, may then be compared with similar data from previously identified mask reflection components such as that contained in a memory or database of mask reflection components.

As explained above, the RPT device 40 may provide data for the type of patient interface as well as operational data. The operational data may be correlated with the mask type and data relating to the patient to determine whether a particular mask type is effective. For example, the operational data reflects both the use times of the RPT device 40 as well as whether the use provides effective therapy. Types of patient interfaces may be correlated with the level of patient compliance or effectiveness of therapy as determined from the operational data collected by the RPT device 40. The correlated data may be used to better determine an effective interface for new patients requiring respiratory therapy from a similar RPT device. This selection is combined with facial dimensions obtained from a scan of the face of the new patient to assist in the selection of an interface.

Thus, the present technology allows patients to more quickly and conveniently obtain a patient interface such as a mask by integrating data gathered from use of RPT devices in relation to different masks by a patient population with facial features of the individual patient determined by a scanning process. A scanning process allows a patient quickly measure their facial anatomy from the comfort of their own home using a computing device, such as a desktop computer, tablet, smart phone or other mobile device. The computing device may then receive a recommendation for an appropriate patient interface size and type after analysis of the facial dimensions of the patient and data from a general patient population relating to different interfaces. Facial data may also be gathered in other ways such as from pre-stored facial images. Such facial data is stored and correlated with information relating to the patient and operational data from the RPT device.

In this example, an application downloadable from a manufacturer or third party server to a smartphone or tablet with an integrated camera may be used to collect facial data. When launched, the application may provide visual and/or audio instructions. As instructed, the user (i.e. a patient) may stand in front of a mirror, and press the camera button on a user interface. An activated process may then take a series of pictures of the user's face, and then, within a matter of seconds for example, obtain facial dimensions for selection of an interface (based on the processor analyzing the pictures). As will be explained below, such an application may be used to collect feedback from a user once a mask is selected and used in conjunction with the RPT 40.

A user/patient may capture an image or series of images of their facial structure. Instructions provided by an application stored on a computer-readable medium, such as when executed by a processor, detect various facial landmarks within the images, measure and scale the distance between such landmarks, compare these distances to a data record, and recommend an appropriate patient interface size. Thus, an automated device of a consumer may permit accurate patient interface selection, such as in the home, to permit customers to determine sizing without trained associates.

Figure 5:
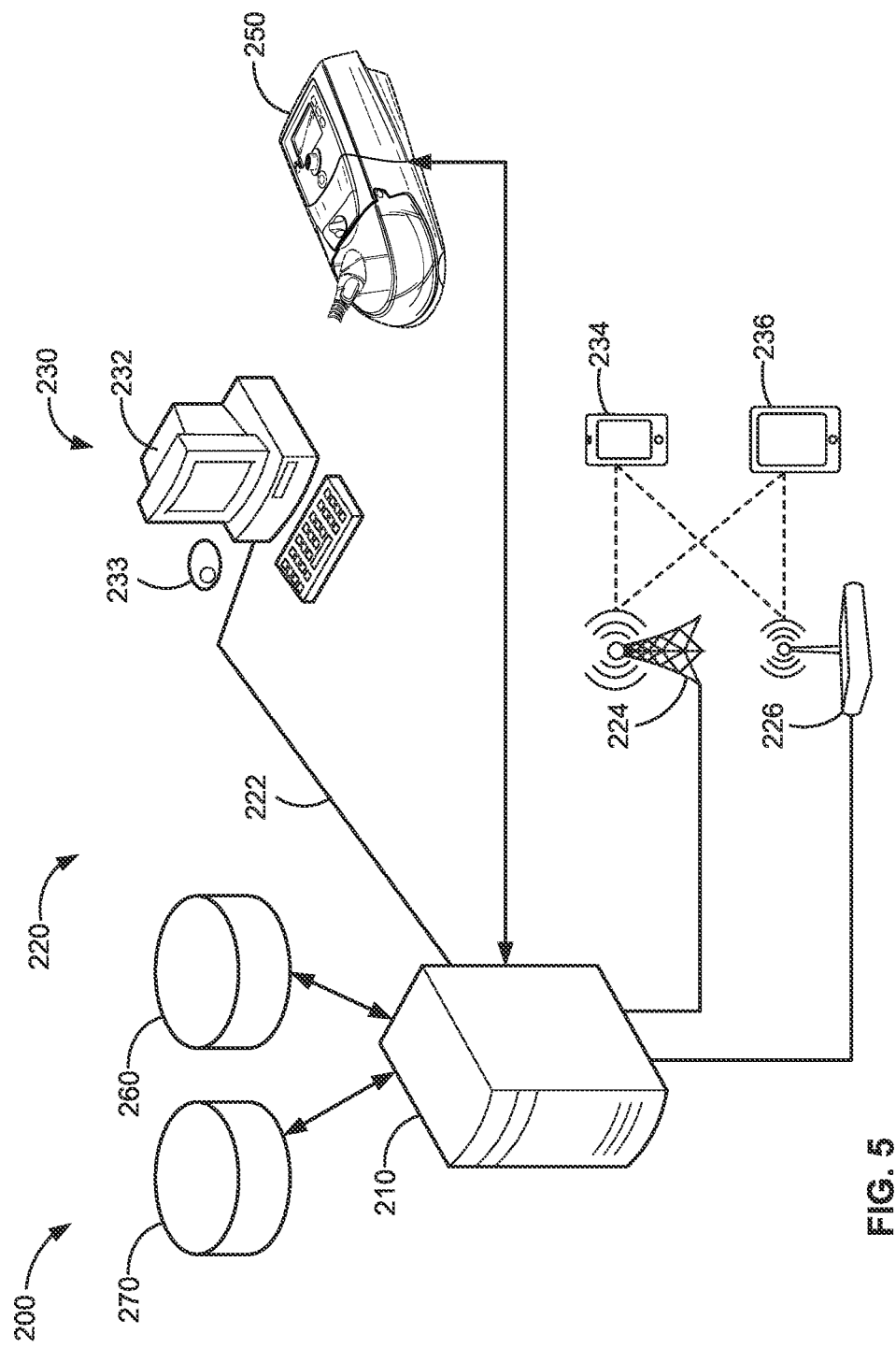
FIG. 5 is a diagram of an example system for collecting patient data relating to a patient interface which includes a computing device.

FIG. 5 depicts an example system 200 that may be implemented for collecting patient interface feedback data from patients. The system 200 may also include automatic facial feature measuring and patient interface selection. System 200 may generally include one or more of servers 210, a communication network 220, and a computing device 230. Server 210 and computing device 230 may communicate via a communication network 220, which may be a wired network 222, wireless network 224, or wired network with a wireless link 226. In some versions, server 210 may communicate one-way with computing device 230 by providing information to computing device 230, or vice versa. In other embodiments, server 210 and computing device 230 may share information and/or processing tasks. The system 200 may be implemented, for example, to permit automated purchase of patient interfaces such as the mask 100 in FIG. 1 where the process may include automatic sizing processes described in more detail herein. For example, a customer may order a mask online after running a mask selection process that automatically identifies a suitable mask size by image analysis of the customer's facial features in combination with operational data from other masks and RPT operational data from a patient population using different types and sizes of masks. The system 200 will continue to collect feedback data after the mask is used by a patient.

The server 210 and or the computing device 230 may also be in communication with a respiratory therapy device such as an RPT 250 similar to the RPT 40 shown in FIG. 1. The RPT device 250 in this example collects operational data in relation to patient use, mask leaks, and other relevant data to provide feedback in relation to mask use. The data from the RPT devices 250 is collected and correlated with the individual patient data of the patient using the RPT devices 250 in a patient database 260. A patient interface database 270 includes data on different types and sizes of interfaces such as masks that may be available for a new patient. The patient interface database 270 may also include acoustic signature data of each type of mask that may enable the determination of mask type from audio data collected from respiratory therapy devices. A mask analysis engine executed by the server 210 is used to correlate and determine effective mask sizes and shapes from the individual facial dimensional data and corresponding effectiveness from operational data collected by the RPT devices 250 encompassing an entire patient population. For example, an effective fit may be evidenced by minimum detected leaks, maximum compliance with a therapy plan (e.g., mask on and off times and frequency of on and off events), number of apneas overnight, AHI levels, pressure settings used on their device and also prescribed pressure settings. This data may be correlated with facial dimensional data for a new patient. As will be explained, the server 210 collects the data from multiple patients stored in the database 260 and corresponding mask size and type data stored in the database 270 to select an appropriate mask based on the optimal mask that best fits the scanned facial dimensional data collected from the new patient and the masks that achieved the best operational data for patients that have facial dimensions, sleep behavioral data, and demographic data that are similar to the new patient. Such data is supplemented by additional feedback in the form of subjective data entered by a patient using the RPT device 250 as well as operational data from the RPT device 250 related to the patient interface or mask.

Figure 6:
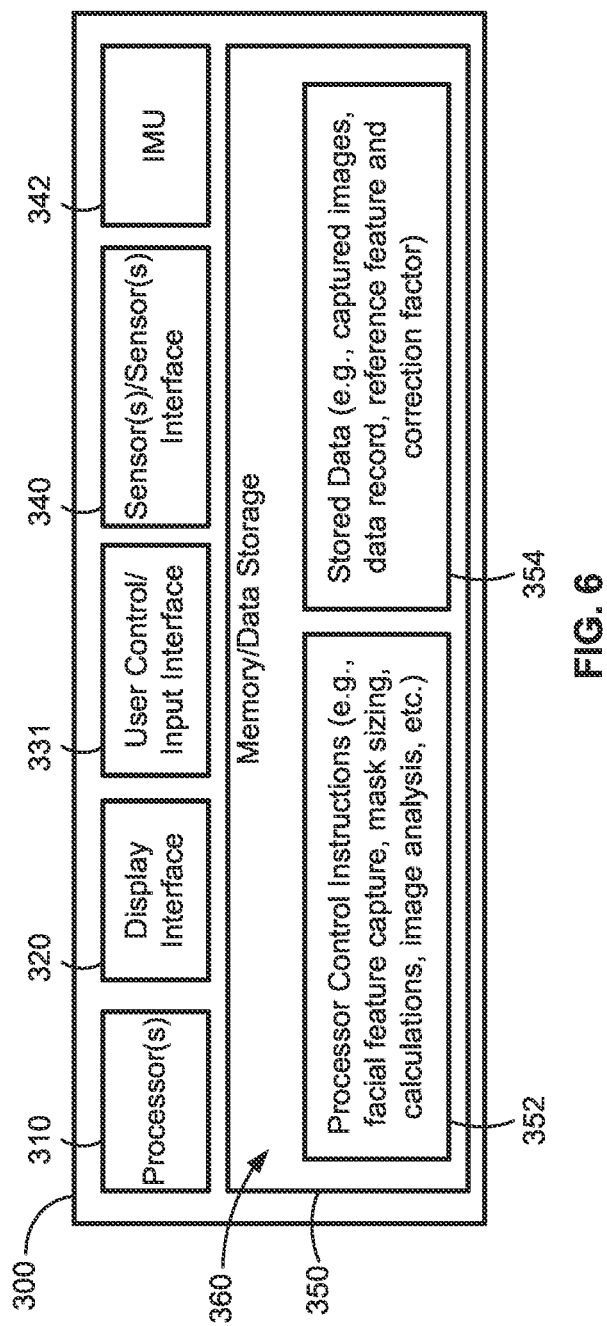
FIG. 6 is a diagram of the components of a computing device used to capture facial data.

The computing device 230 can be a desktop or laptop computer 232 or a mobile device, such as a smartphone 234 or tablet 236. FIG. 6 depicts the general architecture 300 of the computing device 230. The computing device 230 may include one or more processors 310. The computing device 230 may also include a display interface 320, user control/input interface 331, sensor 340 and/or a sensor interface for one or more sensor(s), inertial measurement unit (IMU) 342 and non-volatile memory/data storage 350.

Sensor 340 may be one or more cameras (e.g., a CCD charge-coupled device or active pixel sensors) that are integrated into computing device 230, such as those provided in a smartphone or in a laptop. Alternatively, where the computing device 230 is a desktop computer, device 230 may include a sensor interface for coupling with an external camera, such as the webcam 233 depicted in FIG. 5. Other exemplary sensors that could be used to assist in the methods described herein that may either be integral with or external to the computing device include stereoscopic cameras, for capturing three-dimensional images, or a light detector capable of detecting reflected light from a laser or strobing/structured light source.

User control/input interface 331 allows the user to provide commands or respond to prompts or instructions provided to the user. This could be a touch panel, keyboard, mouse, microphone, and/or speaker, for example.

The display interface 320 may include a monitor, LCD panel, or the like to display prompts, output information (such as facial measurements or interface size recommendations), and other information, such as a capture display, as described in further detail below.

Memory/data storage 350 may be the computing device's internal memory, such as RAM, flash memory or ROM. In some embodiments, memory/data storage 350 may also be external memory linked to computing device 230, such as an SD card, server, USB flash drive or optical disc, for example. In other embodiments, memory/data storage 350 can be a combination of external and internal memory. Memory/data storage 350 includes stored data 354 and processor control instructions 352 that instruct processor 310 to perform certain tasks. Stored data 354 can include data received by sensor 340, such as a captured image, and other data that is provided as a component part of an application. Processor control instructions 352 can also be provided as a component part of an application.

As explained above, a facial image may be captured by a mobile computing device such as the smartphone 234. An appropriate application executed on the computing device 230 or the server 210 can provide three-dimensional relevant facial data to assist in selection of an appropriate mask. The application may use any appropriate method of facial scanning Such applications may include the Capture from StandardCyborg (https://www.standardcyborg.com/), an application from Scandy Pro (https://www.scandy.co/products/scandy-pro), the Beauty3D application from Qianxun3d (http://www.qianxun3d.com/scanpage), the Unre 3D Face-App (http://www.unre.ai/index.php?route=ios/detail) and an application from Bellus3D (https://www.bellus3d.com/) A detailed process of facial scanning include the techniques disclosed in WO 2017000031, hereby incorporated by reference in its entirety.

One such application is an application for facial feature measuring and/or patient data collection 360, which may be an application downloadable to a mobile device, such as smartphone 234 and/or tablet 236. The application 360 may also collect facial features and data of patients who have already been using masks for better collection of feedback from such masks. The application 360, which may be stored on a computer-readable medium, such as memory/data storage 350, includes programmed instructions for processor 310 to perform certain tasks related to facial feature measuring and/or patient interface sizing. The application also includes data that may be processed by the algorithm of the automated methodology. Such data may include a data record, reference feature, and correction factors, as explained in additional detail below.

The application 360 is executed by the processor 310, to measure patient facial features using two-dimensional or three-dimensional images and to select appropriate patient interface sizes and types, such as from a group of standard sizes, based on the resultant measurements. The method may generally be characterized as including three or four different phases: a pre-capture phase, a capture phase, a post-capture image processing phase, and a comparison and output phase.

In some cases, the application for facial feature measuring may control a processor 310 to output a visual display that includes a reference feature on the display interface 320. The user may position the feature adjacent to their facial features, such as by movement of the camera. The processor may then capture and store one or more images of the facial features in association with the reference feature when certain conditions, such as alignment conditions are satisfied. This may be done with the assistance of a mirror. The mirror reflects the displayed reference feature and the user's face to the camera. The application then controls the processor 310 to identify certain facial features within the images and measure distances therebetween. By image analysis processing a scaling factor may then be used to convert the facial feature measurements, which may be pixel counts, to standard mask measurement values based on the reference feature. Such values may be, for example, standardized unit of measure, such as a meter or an inch, and values expressed in such units suitable for mask sizing.

Additional correction factors may be applied to the measurements. The facial feature measurements may be compared to data records that include measurement ranges corresponding to different patient interface sizes for particular patient interface forms, such as nasal masks and FFMs, for example. The recommended size may then be chosen and be output to the user/patient based on the comparison(s) as a recommendation. Such a process may be conveniently effected within the comfort of any preferred user location. The application may perform this method within seconds. In one example, the application performs this method in real time.

In the pre-capture phase, the processor 310, among other things, assists the user in establishing the proper conditions for capturing one or more images for sizing processing. Some of these conditions include proper lighting and camera orientation and motion blur caused by an unsteady hand holding the computing device 230, for example.

A user may conveniently download an application for performing the automatic measuring and sizing at computing device 230 from a server, such as a third party application-store server, onto their computing device 230. When downloaded, such application may be stored on the computing device's internal non-volatile memory, such as RAM or flash memory. Computing device 230 is preferably a mobile device, such as smartphone 234 or tablet 236.

When the user launches the application, the processor 310 may prompt the user via the display interface 320 to provide patient specific information, such as age, gender, weight, and height. However, the processor 310 may prompt to the user to input this information at any time, such as after the user's facial features are measured and after the user uses the mask with the RPT. The processor 310 may also present a tutorial, which may be presented audibly and/or visually, as provided by the application to aid the user in understanding their role during the process. The prompts may also require information for patient interface type, e.g. nasal or full face, etc. and of the type of device for which the patient interface will be used. Also, in the pre-capture phase, the application may extrapolate the patient specific information based on information already gathered by the user, such as after receiving captured images of the user's face, and based on machine learning techniques or through artificial intelligence. Other information may also be collected through interfaces as will be explained below.

When the user is prepared to proceed, which may be indicated by a user input or response to a prompt via user control/input interface 331, the processor 310 activates the sensor 340 as instructed by the processor control instructions 352. The sensor 340 is preferably the mobile device's forward facing camera, which is located on the same side of the mobile device as display interface 320. The camera is generally configured to capture two-dimensional images. Mobile device cameras that capture two-dimensional images are ubiquitous. The present technology takes advantage of this ubiquity to avoid burdening the user with the need to obtain specialized equipment.

Around the same time the sensor/camera 340 is activated, the processor 310, as instructed by the application, presents a capture display on the display interface 320. The capture display may include a camera live action preview, a reference feature, a targeting box, and one or more status indicators or any combination thereof. In this example, the reference feature is displayed centered on the display interface and has a width corresponding to the width of the display interface 320. The vertical position of the reference feature may be such that the top edge of reference feature abuts the upper most edge of the display interface 320 or the bottom edge of reference feature abuts the lower most edge of the display interface 320. A portion of the display interface 320 will display the camera live action preview 324, typically showing the user's facial features captured by the sensor/camera 340 in real time if the user is in the correct position and orientation.

The reference feature is a feature that is known to computing device 230 (predetermined) and provides a frame of reference to processor 310 that allows processor 310 to scale captured images. The reference feature may preferably be a feature other than a facial or anatomical feature of the user. Thus, during the image processing phase, the reference feature assists processor 310 in determining when certain alignment conditions are satisfied, such as during the pre-capture phase. The reference features may be a quick response (QR) code or known exemplar or marker, which can provide processor 310 certain information, such as scaling information, orientation, and/or any other desired information which can optionally be determined from the structure of the QR code. The QR code may have a square or rectangular shape. When displayed on display interface 320, the reference feature has predetermined dimensions, such as in units of millimeters or centimeters, the values of which may be coded into the application and communicated to processor 310 at the appropriate time. The actual dimensions of reference feature 326 may vary between various computing devices. In some versions, the application may be configured to be a computing device model-specific in which the dimensions of reference feature 326, when displayed on the particular model, is already known. However, in other embodiments, the application may instruct processor 310 to obtain certain information from device 230, such as display size and/or zoom characteristics that allow the processor 310 to compute the real world/actual dimensions of the reference feature as displayed on display interface 320 via scaling. Regardless, the actual dimensions of the reference feature as displayed on the display interfaces 320 of such computing devices are generally known prior to post-capture image processing.

Along with the reference feature, the targeting box may be displayed on display interface 320. The targeting box allows the user to align certain components within capture display 322 in targeting box, which is desired for successful image capture.

The status indicator provides information to the user regarding the status of the process. This helps ensure the user does not make major adjustments to the positioning of the sensor/camera prior to completion of image capture.

Thus, when the user holds display interface 320 parallel to the facial features to be measured and presents user display interface 320 to a mirror or other reflective surface, the reference feature is prominently displayed and overlays the real-time images seen by camera/sensor 340 and as reflected by the mirror. This reference feature may be fixed near the top of display interface 320. The reference feature is prominently displayed in this manner at least partially so that sensor 340 can clearly see the reference feature so that processor 310 can easily the identify feature. In addition, the reference feature may overlay the live view of the user's face, which helps avoid user confusion.

The user may also be instructed by processor 310, via display interface 320, by audible instructions via a speaker of the computing device 230, or be instructed ahead of time by the tutorial, to position display interface 320 in a plane of the facial features to be measured. For example, the user may be instructed to position display interface 320 such that it is facing anteriorly and placed under, against, or adjacent to the user's chin in a plane aligned with certain facial features to be measured. For example, display interface 320 may be placed in planar alignment with the sellion and suprementon. As the images ultimately captured are two-dimensional, planar alignment helps ensure that the scale of reference feature 326 is equally applicable to the facial feature measurements. In this regard, the distance between the mirror and both of the user's facial features and the display will be approximately the same.

When the user is positioned in front of a mirror, and the display interface 320, which includes the reference feature, is roughly placed in planar alignment with the facial features to be measured, the processor 310 checks for certain conditions to help ensure sufficient alignment. One exemplary condition that may be established by the application, as previously mentioned, is that the entirety of the reference feature must be detected within targeting box 328 in order to proceed. If the processor 310 detects that the reference feature is not entirely positioned within targeting box, the processor 310 may prohibit or delay image capture. The user may then move their face along with display interface 320 to maintain planarity until the reference feature, as displayed in the live action preview, is located within targeting box. This helps optimized alignment of the facial features and display interface 320 with respect to the mirror for image capture.

When processor 310 detects the entirety of reference feature within targeting box, processor 310 may read the IMU 342 of the computing device for detection of device tilt angle. The IMU 342 may include an accelerometer or gyroscope, for example. Thus, the processor 310 may evaluate device tilt such as by comparison against one or more thresholds to ensure it is in a suitable range. For example, if it is determined that computing device 230, and consequently display interface 320 and user's facial features, is tilted in any direction within about ±5 degrees, the process may proceed to the capture phase. In other embodiments, the tilt angle for continuing may be within about ±10 degrees, ±7 degrees, ±3 degrees, or ±1 degree. If excessive tilt is detected a warning message may be displayed or sounded to correct the undesired tilt. This is particularly useful for assisting the user to help prohibit or reduce excessive tilt, particularly in the anterior-posterior direction, which if not corrected, could pose as a source of measuring error as the captive reference image will not have a proper aspect ratio.

When alignment has been determined by the processor 310 as controlled by the application, the processor 310 proceeds into the capture phase. The capture phase preferably occurs automatically once the alignment parameters and any other conditions precedent are satisfied. However, in some embodiments, the user may initiate the capture in response to a prompt to do so.

When image capture is initiated, the processor 310 via the sensor 340 captures a number n of images, which is preferably more than one image. For example, the processor 310 via the sensor 340 may capture about 5 to 20 images, 10 to 20 images, or 10 to 15 images, etc. The quantity of images captured may be time-based. In other words, the number of images that are captured may be based on the number of images of a predetermined resolution that can be captured by sensor 340 during a predetermined time interval. For example, if the number of images sensor 340 can capture at the predetermined resolution in 1 second is 40 images and the predetermined time interval for capture is 1 second, the sensor 340 will capture 40 images for processing with the processor 310. The quantity of images may be user-defined, determined by the server 210 based on artificial intelligence or machine learning of environmental conditions detected, or based on an intended accuracy target. For example, if high accuracy is required then more captured images may be required. Although, it is preferable to capture multiple images for processing, one image is contemplated and may be successful for use in obtaining accurate measurements. However, more than one image allows average measurements to be obtained. This may reduce error/inconsistencies and increase accuracy. The images may be placed by the processor 310 in the stored data 354 of the memory/data storage 350 for post-capture processing.

Once the images are captured, the images are processed by processor 310 to detect or identify facial features/landmarks and measure distances therebetween. The resultant measurements may be used to recommend an appropriate patient interface size. This processing may alternatively be performed by server 210 receiving the transmitted captured images and/or on the user's computing device (e.g., smart phone). Processing may also be undertaken by a combination of the processor 310 and the server 210. In one example, the recommended patient interface size may be predominantly based on the user's nose width. In other examples, the recommended patient interface size may be based on the user's mouth and/or nose dimensions.

The processor 310, as controlled by the application, retrieves one or more captured images from the stored data 354. The image is then extracted by the processor 310 to identify each pixel comprising the two-dimensional captured image. The processor 310 then detects certain pre-designated facial features within the pixel formation.

Detection may be performed by the processor 310 using edge detection, such as Canny, Prewitt, Sobel, or Robert's edge detection, for example. These edge detection techniques/algorithms help identify the location of certain facial features within the pixel formation, which correspond to the patient's actual facial features as presented for image capture. For example, the edge detection techniques can first identify the user's face within the image and also identify pixel locations within the image corresponding to specific facial features, such as each eye and borders thereof, the mouth and corners thereof, left and right alares, sellion, supramenton, glabella and left and right nasolabial sulci, etc. The processor 310 may then mark, tag or store the particular pixel location(s) of each of these facial features. Alternatively, or if such detection by the processor 310/server 210 is unsuccessful, the pre-designated facial features may be manually detected and marked, tagged or stored by a human operator with viewing access to the captured images through a user interface of the processor 310/server 210.

Once the pixel coordinates for these facial features are identified, the application controls the processor 310 to measure the pixel distance between certain of the identified features. For example, the distance may generally be determined by the number of pixels for each feature and may include scaling. For example, measurements between the left and right alares may be taken to determine pixel width of the nose and/or between the sellion and supramenton to determine the pixel height of the face. Other examples include pixel distance between each eye, between mouth corners, and between left and right nasolabial sulci to obtain additional measurement data of particular structures like the mouth. Further distances between facial features can be measured. In this example, certain facial dimensions are used for the patient interface selection process.

Once the pixel measurements of the pre-designated facial features are obtained, an anthropometric correction factor(s) may be applied to the measurements. It should be understood that this correction factor can be applied before or after applying a scaling factor, as described below. The anthropometric correction factor can correct for errors that may occur in the automated process, which may be observed to occur consistently from patient to patient. In other words, without the correction factor, the automated process, alone, may result in consistent results from patient to patient, but results that may lead to a certain amount of mis-sized patient interfaces. The correction factor, which may be empirically extracted from population testing, shifts the results closer to a true measurement helping to reduce or eliminate mis-sizing. This correction factor can be refined or improved in accuracy over time as measurement and sizing data for each patient is communicated from respective computing devices to the server 210 where such data may be further processed to improve the correction factor. The anthropometric correction factor may also vary between the forms of patient interfaces. For instance, the correction factor for a particular patient seeking an FFM may be different from the correction factor when seeking a nasal mask. Such a correction factor may be derived from tracking of mask purchases, such as by monitoring mask returns and determining the size difference between a replacement mask and the returned mask.

In order to apply the facial feature measurements to patient interface sizing, whether corrected or uncorrected by the anthropometric correction factor, the measurements may be scaled from pixel units to other values that accurately reflect the distances between the patient's facial features as presented for image capture. The reference feature may be used to obtain a scaling value or values. Thus, the processor 310 similarly determines the reference feature's dimensions, which can include pixel width and/or pixel height (x and y) measurements (e.g., pixel counts) of the entire reference feature. More detailed measurements of the pixel dimensions of the many squares/dots that comprise a QR code reference feature, and/or pixel area occupied by the reference feature and its constituent parts may also be determined. Thus, each square or dot of the QR code reference feature may be measured in pixel units to determine a scaling factor based on the pixel measurement of each dot and then averaged among all the squares or dots that are measured, which can increase accuracy of the scaling factor as compared to a single measurement of the full size of the QR code reference feature. However, it should be understood that whatever measurements are taken of the reference feature, the measurements may be utilized to scale a pixel measurement of the reference feature to a corresponding known dimension of the reference feature.

Once the measurements of the reference feature are taken by the processor 310, the scaling factor is calculated by the processor 310 as controlled by the application. The pixel measurements of reference feature are related to the known corresponding dimensions of the reference feature, e.g. the reference feature 326 as displayed by the display interface 320 for image capture, to obtain a conversion or scaling factor. Such a scaling factor may be in the form of length/pixel or area/pixel$^2$. In other words, the known dimension(s) may be divided by the corresponding pixel measurement(s) (e.g., count(s)).

The processor 310 then applies the scaling factor to the facial feature measurements (pixel counts) to convert the measurements from pixel units to other units to reflect distances between the patient's actual facial features suitable for mask sizing. This may typically involve multiplying the scaling factor by the pixel counts of the distance(s) for facial features pertinent for mask sizing.

These measurement steps and calculation steps for both the facial features and reference feature are repeated for each captured image until each image in the set has facial feature measurements that are scaled and/or corrected.

The corrected and scaled measurements for the set of images may then optionally be averaged by the processor 310 to obtain final measurements of the patient's facial anatomy. Such measurements may reflect distances between the patient's facial features.

In the comparison and output phase, results from the post-capture image processing phase may be directly output (displayed) to a person of interest or compared to data record(s) to obtain an automatic recommendation for a patient interface size.

Once all of the measurements are determined, the results (e.g., averages) may be displayed by the processor 310 to the user via the display interface 320. In one embodiment, this may end the automated process. The user/patient can record the measurements for further use by the user.

Alternatively, the final measurements may be forwarded either automatically or at the command of the user to the server 210 from the computing device 230 via the communication network 220. The server 210 or individuals on the server-side may conduct further processing and analysis to determine a suitable patient interface and patient interface size.

In a further embodiment, the final facial feature measurements that reflect the distances between the actual facial features of the patient are compared by the processor 310 to patient interface size data such as in a data record. The data record may be part of the application for automatic facial feature measurements and patient interface sizing. This data record can include, for example, a lookup table accessible by the processor 310, which may include patient interface sizes corresponding to a range of facial feature distances/values. Multiple tables may be included in the data record, many of which may correspond to a particular form of patient interface and/or a particular model of patient interface offered by the manufacturer.

The example process for selection of patient interfaces identifies key landmarks from the facial image captured by the above mentioned method. In this example, initial correlation to potential interfaces involves facial landmarks including face height, nose width and nose depth as represented by lines 3010, 3020 and 3030 in FIGS. 3A-3B. These three facial landmark measurements are collected by the application to assist in selecting the size of a compatible mask such as through the lookup table or tables described above.

As explained above, operational data of each RPT may be collected for a large population of patients after a mask has been selected or specifically manufactured for a patient. This may include usage data based on when each patient operates the RPT. Thus, compliance data such as how long and often a patient uses the RPT over a predetermined period of time may be determined from the collected operational data. Leak data may be determined from the operational data such as analysis of flow rate data or pressure data. Mask switching data using analysis of acoustic signals may be derived to determine whether the patient is switching masks. The RPT may be operational to determine the mask type based on an internal or external audio sensor such as the microphone 4278 in FIG. 4B with cepstrum analysis as explained above. Alternatively, with older masks, operational data may be used to determine the type of mask through correlation of collected acoustic data to the acoustic signatures of known masks.

In this example, patient input of feedback data may be collected via a user application executed on the computing device 230 or the smartphone 234. The user application may be part of the user application 360 that instructs the user to obtain the facial landmark features or a separate application. This may also include subjective data obtained via a questionnaire with questions to gather data on comfort preferences, whether the patient is a mouth or nose breather (for example, a question such as "Do you wake up with a dry mouth?"), and mask material preferences such as silicone, foam, textile, gel for example. For example, patient input may be gathered through a patient responding to subjective questions via the user application in relation to the comfort of the patient interface. Other questions may relate to relevant user behavior such as sleep characteristics. For example, the subjective questions can include questions such as do you wake up with a dry mouth?, are you a mouth breather?, or what are your comfort preferences? Such sleep information may include sleep hours, how a user sleeps, and outside effects such as temperature, stress factors, etc. Subjective data may be as simple as a numerical rating as to comfort or more detailed response. Such subjective data may also be collected from a graphical interface. For example, selected leaks from an interface may be collected from a user selecting parts of a graphic of the selected interface. The collected patient input data may be assigned to the patient database 260 in FIG. 6. The subjective input data from patients may be used as feedback for mask designs and features for future reference. Other subjective data may be collected related to the psychological safety of the patient. For example, questions such as whether the patient feels claustrophobic with that specific mask or how psychologically comfortable does the patient feel wearing the mask next to their bed partner may be asked and inputs may be collected.

Other data sources may collect data outside of use of the RPT that may be correlated to a particular mask. This may include patient demographic data such as age, gender or location; AHI severity indicating level of sleep apnea experienced by the patient. Other data may be the prescribed pressure settings for new patients of the RPT device.

After selection of the mask, the system 200 continues to collect operational data from the RPT 250. The collected data is added to the databases 260 and 270. The feedback from new patients may be used to refine recommendations for better mask options. For example, if operational data determines that a recommended mask has a high level of leaks, another mask type may be recommended to the patient. Through a feedback loop, the selection algorithm may be refined to learn particular aspects of facial geometry that may be best suited to a particular mask. This correlation may be used to refine the recommendation of a mask to a new patient with that facial geometry. The collected data and correlated mask type data may thus provide additional updating to the selection and design criteria for masks. Thus, the system may provide additional insights for improving selection or design of a mask for a patient.

In addition to mask selection, the system may allow analysis of mask selection in relation to respiratory therapy effectiveness and compliance. The additional data allows optimization of the respiratory therapy based on data through a feedback loop.

Machine learning may be applied to provide correlations between mask types and characteristics, and increasing compliance with respiratory therapy. The correlations may be employed to select or design characteristics for new mask designs. Such machine learning may be executed by the server 210. The mask analysis algorithm may be learned with a training data set based on the outputs of favorable operational results and inputs including patient demographics, mask sizes and types, and subjective data collected from patients. Machine learning may be used to discover correlation between desired mask characteristics and predictive inputs such as facial dimensions, patient demographics, operational data from the RPT devices, and environmental conditions. Machine learning may employ techniques such as neural networks, clustering or traditional regression techniques. Test data may be used to test different types of machine learning algorithms and determine which one has the best accuracy in relation to predicting correlations.

The model for selection of an optimal interface may be continuously updated by new input data from the system in FIG. 5. Thus, the model may become more accurate with greater use by the analytics platform.

As explained above, one part of the system in FIG. 5 relates to recommending an interface for patients using the RPTs. A second function of the system is a feedback data collection process that collects data for future mask design or adjustment. Once the patient has been provided a recommended mask and has used it for a period of time, such as two days, two weeks, or another period of time, the system can monitor RPT usage and collect other data. Based on this collected data, if the mask is not performing to a high standard as determined from adverse data indicating leaks, dropping compliance, or unsatisfactory feedback, the system can re-evaluate the mask selection, and update the database 260 and machine learning algorithm with the results for the patient. The system may then recommend a new mask to suit the new collected data. For example, if a relatively high leak rate is determined from data based off acoustic signatures or other sensors, the patient may be jaw dropped during REM sleep, which may signal the need for a different type of interface such as a full face mask rather than an initially selected nasal only or smaller full face mask.

The system may also adjust the recommendation in response to satisfactory follow up data. For example, if operational data indicates an absence of leaks from a selected full face mask, the routine may recommend trying a smaller mask for a better experience. Tradeoffs between style, materials, variations, correlations with patient preference to maximize compliance may be used to provide follow up recommendations. The tradeoffs for an individual patient may be determined through a tree of inputs that are displayed to the patient by the application. For example, if a patient indicates skin irritation is a problem from a menu of potential problems, a graphic with locations of the potential irritation on a facial image may be displayed to collect data as the specific location of irritation from the patient. The specific data may provide better correlation to the optimal mask for the particular patient.

The present process allows for collection of feedback data and correlation with facial feature data to provide mask designers data for designing other masks. As part of the application 360 that collects facial data or another application executed by a computing device such as the computing device 230 or the mobile device 234 in FIG. 5, feedback information relating to the mask may be collected.

The application 360 may collect initial patient information and provide security measures to protect data such as setting up passwords and the like. Once a patient sets up the application and correlates the application 360 to the specific patient identity, the application may collect the feedback data.

Figures 7A, 7B, 7C, 7D:
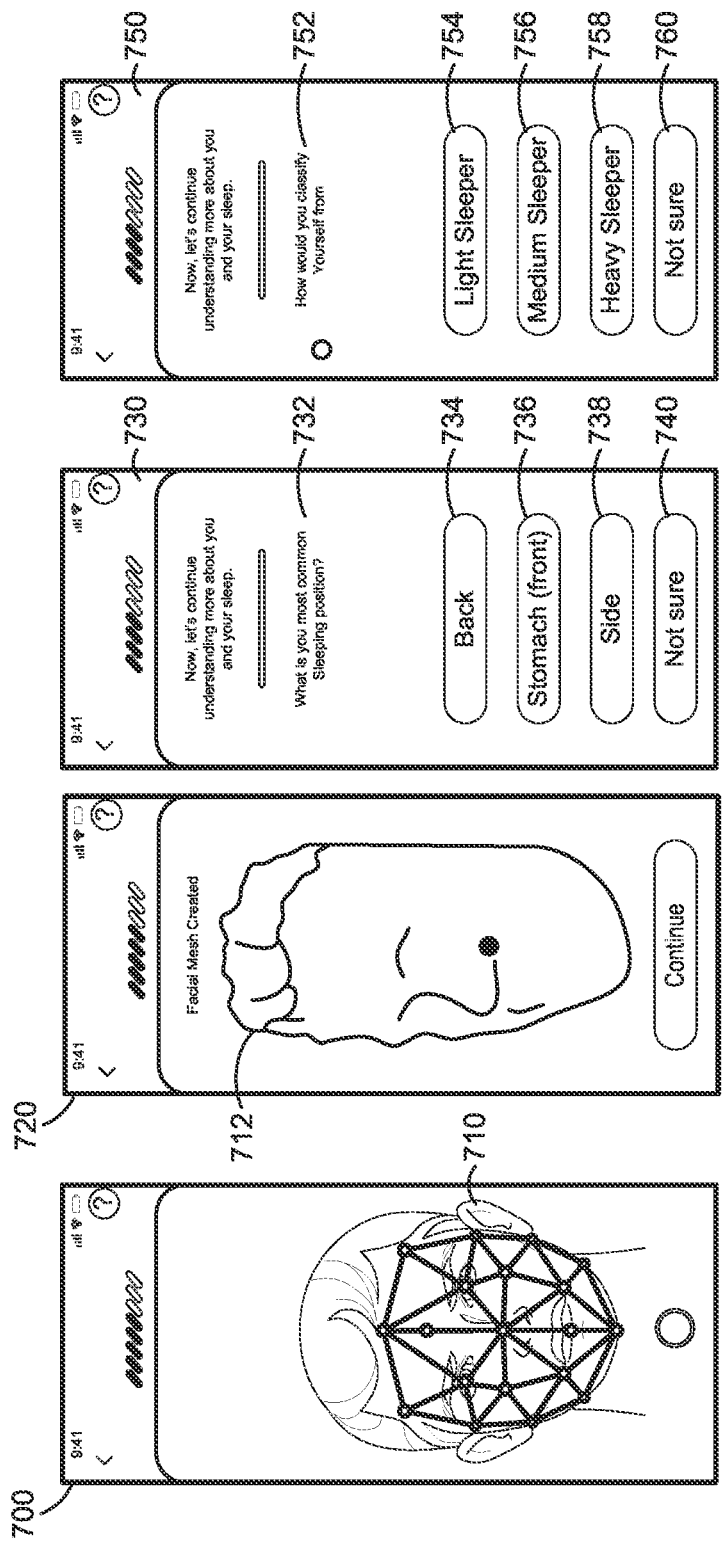
FIG. 7A is an example interface that may permit a facial scan to create a facial image for capturing facial data.
FIG. 7B is an example interface that shows a facial mesh interposed on the facial image in FIG. 7A for data collection of facial measurements.
FIG. 7C is an example sleep position data collection interface.
FIG. 7D is an example sleep type data collection interface.

If facial data has already been gathered for the patient, the application 360 will proceed to collect other data. If no previous facial data has been collected for the patient, the application 360 will provide an option to the patient for collecting facial data. FIG. 7A shows an interface 700 of the application that shows a facial image 710. The patient may capture the facial image 710 similar to the facial scanning process described above in relation to mask selection. After the facial image 710 is displayed, a facial mesh may be created. FIG. 7B shows a second interface 720 that displays a facial mesh 712 created from the facial image 710. The facial data may then be derived from the facial mesh 712 and stored, and transmitted to the server 210 for storage the database 260 in FIG. 5.

The application 360 collects all relevant data for evaluating characteristics for mask design from the patient through other interfaces displayed. FIG. 7C shows a sleep data collection interface 730 that allows collection of subjective patient data relating to sleep quality. This data may be collected and correlated to objective sleep data or associated operational data collected by the RPT explained above. The interface 730 includes a question 732 relating to sleep position. The interface 730 includes choices for the user to select including a back selection 734, a stomach selection 736, and a side selection 738. If a user is unsure, they may select an unsure option 740. The interface 730 thus collects sleep position data that is correlated with the particular user.

Another sleep interface 750 shown in FIG. 7D is displayed for collecting the type of sleep. The interface 750 includes a question 752 about sleep type. The interface 750 includes choices for the user to select including a light sleeper selection 754, a medium sleeper selection 756, and a heavy sleeper selection 758. If a user is unsure, they may select an unsure option 760. The interface 750 thus collects sleep type data that is correlated with the particular user.

Figures 8A, 8B, 8C, 8D:
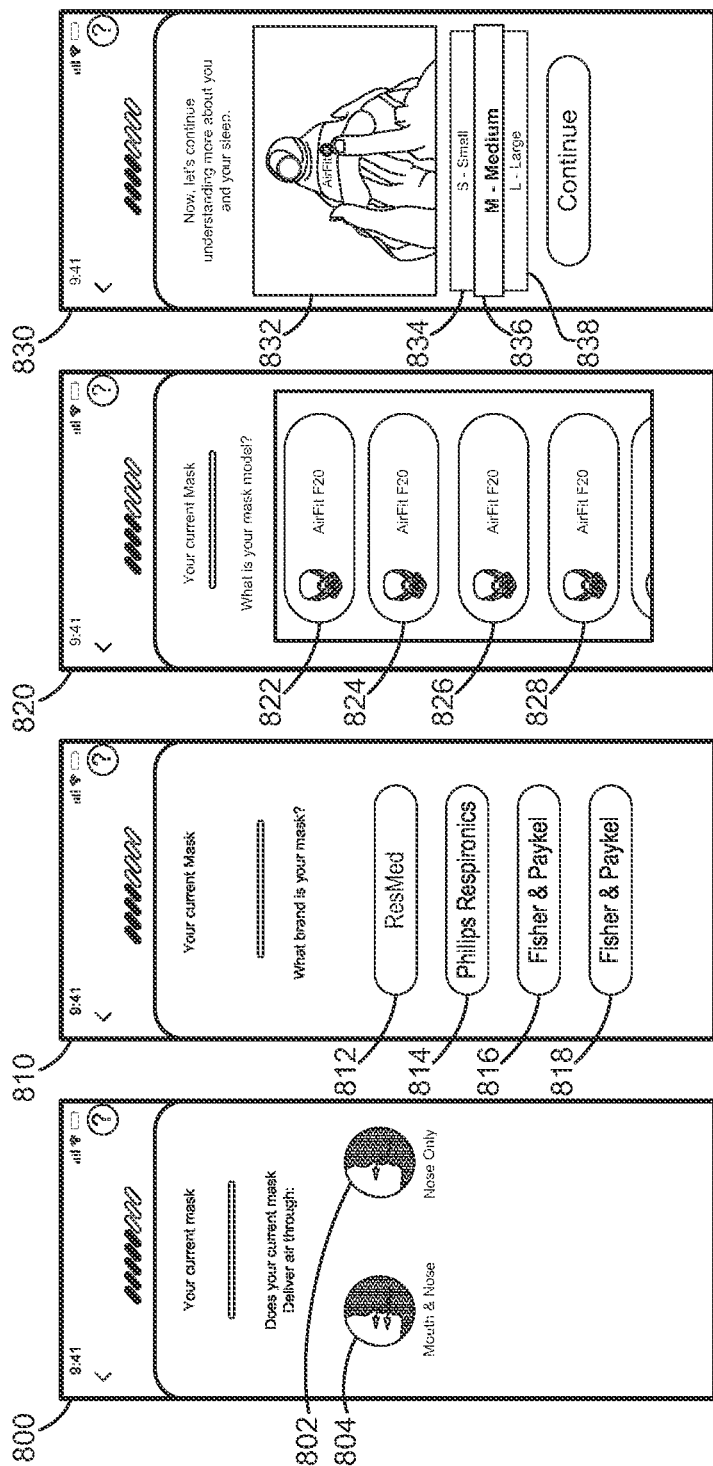
FIG. 8A is an example interface to allow identification of a current mask by nose or mouth/nose type.
FIG. 8B is an example interface to allow identification of the brand of the mask.
FIG. 8C is an example interface to allow identification of a specific mask model.
FIG. 8D is an example interface to allow identification of the mask size.

The application 360 also collects information about the current mask used by the patient. FIG. 8A is an interface 800 that includes selection for a mask that is nose only or nose and mouth. A user thus selects either a selection 802 for a nose only mask or a selection 804 for a nose and mouth mask. In this example, the selections 802 and 804 include helpful graphics for description of the mask type. The selection will dictate further interfaces that are specific to the manufacturer and mask model. After the selection is made by the patient, a mask brand selection interface 810 shown in FIG. 8B is displayed that allows the patient to select the brand of the mask. The interface 810 includes a selection for manufacturer A 812, a selection for manufacturer B 814, a selection for manufacturer C 816, and a selection for manufacturer D 818. The application allows access to all mask models for each of the manufacturers A-D, and will provide this information for subsequent interfaces to allow selection of specific masks of the selected manufacturer A-D.

FIG. 8C shows an interface 820 for the selection of the mask model. The selections in the interface 820 are determined by the manufacturer that is selected in the interface 810 in FIG. 8B. The interface 820 lists selections such as the selections 822, 824, 826, and 828 for each applicable model offered by the manufacturer.

After the mask model is selected, the application 360 displays an interface 830 to determine the size of the cushion of mask as shown in FIG. 8D. The interface 830 includes a graphical image 832 of the model of the mask selected from the interface 820 in FIG. 8C. The graphical image 832 shows the user where to determine the size of the mask. The interface 830 includes a small size selection 834, a medium size selection 836, and a large size selection 838.

Figure 9C:
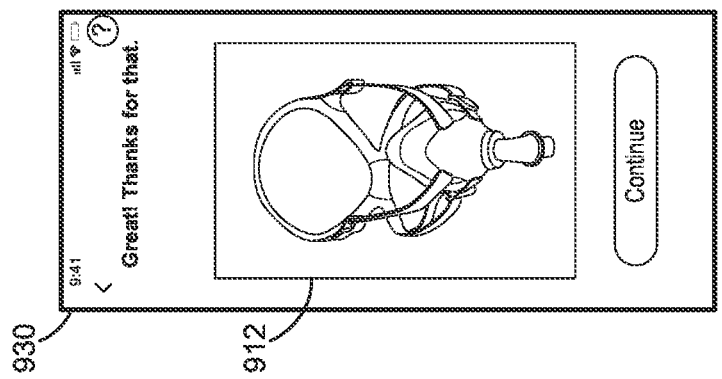
FIG. 9C is a post image capture interface that displays the captured image.
Figure 9B:
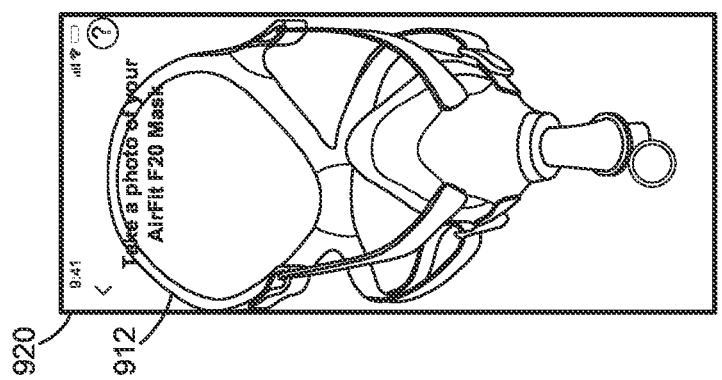
FIG. 9B is an image capture interface for capturing an image of a mask.
Figure 9A:
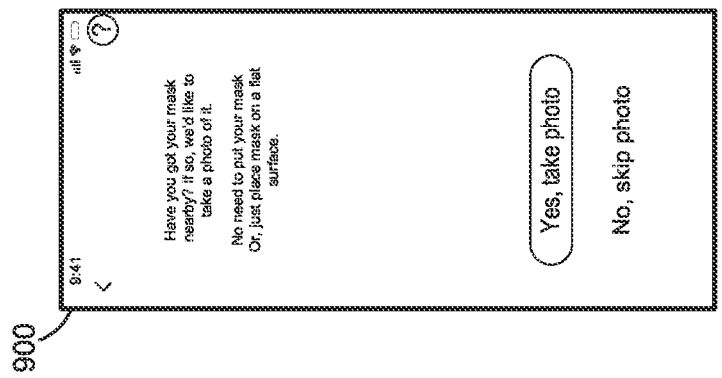
FIG. 9A is an example image instruction interface to allow capturing an image of a mask.

Alternatively, the application 360 may also be programmed to identify a mask by analyzing the obtained graphical image of the mask and comparing the image to identification data relating to known mask models. FIG. 9A shows an instruction interface 900 that provides an option to obtain an automatic visual identification of the mask. FIG. 9B shows a photo interface 910 that allows the capture of an image 912 of the mask. FIG. 9C shows a photo interface 920 that shows the captured image 912 of the mask.

The application 360 also includes interfaces that gather data to determine what masks are used. A short term use interface 930 in FIG. 9D determines whether the mask is the only one used by displaying a question 932 relating to mask use in the last 30 days. The interface 930 may display the graphic of the mask model previously selected by the user. The user may select a yes selection 934 or a no selection 936 indicating other masks have been used. The application 360 may also provide inputs to gather data on previous masks.

FIG. 9E shows a long term use interface 940 that determines whether the mask is the only one used by displaying a question 942 relating to mask use. The interface 940 may display the graphic of the mask model previously selected by the user. The user may select a yes selection 944 or a no selection 946 indicating other masks have been used.

The application 360 also may determine comfort feedback data from the patient. FIG. 10A shows an interface 1000 that determines whether there is any mask discomfort. A question 1002 is displayed asking the patient whether they are experiencing any discomfort from the mask. The patient may select a no option 1004 or a yes option 1006.

If the patient selects the yes option 1006, a visual discomfort identification interface 1010 is displayed as shown in FIG. 10B. The interface 1010 displays an image 1020 of facial features. The image 1020 may be selected from generic facial images accordingly to the sex or other characteristics of the patient. Alternatively, the image 1020 may be the individualized facial image that may be stored on the portable computing device if taken by the application 320, or accessed from a database from previously taken facial images of the patient. A location grid 1022 in the shape of a mask overlays the facial image 1020 of the patient. A selection list 1024 is displayed that describes five areas of potential discomfort including: a) nose bridge; b) top side of nose; c) lower side/corner of nose; d) side/corners of mouth; and e) chin/lower lip. The location grid 1022 includes lines defining five areas 1030, 1032, 1034, 1036, and 1038 corresponding to the areas described in the list 1024 to assist the patient in finding areas of discomfort. Each of the areas 1030, 1032, 1034, 1036, and 1038 represent contact areas between the face and the mask. The user may select one or more areas of discomfort in the list 1024. The listing of the discomfort is then highlighted as well as the corresponding area in the grid 1022. In this example, the location mask is specific to a full face mask, but other types of masks such as a cradle type mask may have a different location grid 1022 with different areas of discomfort specific to the type of the mask.

FIG. 10C shows an example of the interface 1010 when a patient has selected an area of discomfort. In this example, the patient has selected the top side of the nose in the list 1024. This selection is thus highlighted. The area 1032 of the grid 1022 representing the top side of the nose is also highlighted thereby showing the area of discomfort relative to the facial image 1020.

The application 360 also may determine leak feedback data from the patient. FIG. 10D shows an interface 1050 that determines whether there are any air leaks in the seal between the mask and the face. A question 1052 is displayed asking the patient whether they are experiencing any leaks from the mask. The patient may select a no option 1054 or a yes option 1056.

If the patient selects the yes option 1056, a visual discomfort identification interface 1060 is displayed as shown in FIG. TOE. The interface 1060 displays an image 1070 of the patient that may be stored on the portable computing device if taken by the application 320, or accessed from a database from previously taken facial images of the patient. A location grid 1072 in the shape of a mask overlays the facial image 1070 of the patient. A selection list 1074 is displayed that describes five areas of potential air leaks including: a) nose bridge; b) top side of nose; c) lower side/corner of nose; d) side/corners of mouth; and e) chin/lower lip. The location grid 1072 includes lines defining five areas 1080, 1082, 1084, 1086, and 1088 corresponding to the areas described in the list 1074 to assist the patient in finding leaks between the mask and their face in the areas 1080, 1082, 1084, 1086, and 1088, which represent contact areas between the face and the mask. The user may select one or more areas of discomfort in the list 1074. The listing of the discomfort is then highlighted as well as the corresponding area in the grid 1072.

FIG. 10F shows an example of the interface 1060 when a patient has selected an area of discomfort. In this example, the patient has selected to top side of the nose in the list 1074. This selection is thus highlighted. The area 1082 of the grid 1072 is also highlighted thereby showing the area of discomfort relative to the facial image 1070.

FIG. 11A shows an interface 1100 that collects subjective feedback data from a patient as to the impact of an air leak. The interface 1100 is displayed if the user selects the yes option 1056 from the interface 1050 in FIG. 10E. The interface 1100 includes a question 1102 asking a patient to provide a numerical scale input of how much they are bothered by air leaks. The interface 1100 includes a scale 1104 that ranges from 0 (not bothered) to 10 (very bothered). The patient may select a slider 1106 that displays the numerical input from the scale as shown in an image of the interface 1100'. Other similar interfaces may be provided for other questions such as questions related to discomfort in particular areas or regions on the face.

FIG. 11B shows an interface 1150 that collects subjective feedback data from a patient as to their satisfaction with their current mask. The interface 1150 includes a question 1152 asking a patient to provide a numerical rating of the specific mask model of whether they would recommend the mask. The interface 1150 includes a scale 1154 that ranges from 0 (not very likely) to 10 (very likely). The patient may select a slider 1156 that displays the numerical input from the scale as shown in an image of the interface 1150'.

FIG. 11C is an example interface 1160 that may be displayed to collect patient demographic data. The interface 1160 includes an age selection field 1162, a gender selection field 1164, and an ethnicity field 1166. Thus, the patient may use the fields 1162, 1164, and 1166 to enter data for their age, gender and ethnicity. This data may be collected to assist in analysis of mask design relating to patient demographics.

FIG. 11D are example outline graphics that may be interposed for collecting discomfort and air leaks depending on the selected mask type in the interface generated to determine discomfort such as that shown in FIG. 10B or to determine leaks as that shown in FIG. 10C. FIG. 11D shows a series of five different overlay graphics 1170, 1172, 1174, 1776, and 1178 representing the shape of different masks. For example, the overlay graphics 1170, 1176 and 1178 represent different types of nose only masks. The overlay graphics 1172 and 1174 represent different types of mask and nose masks. The appropriate graphic 1170, 1172, 1174, 1776, and 1178 will be interposed based on the selection of the mask by the user.

Figure 12:
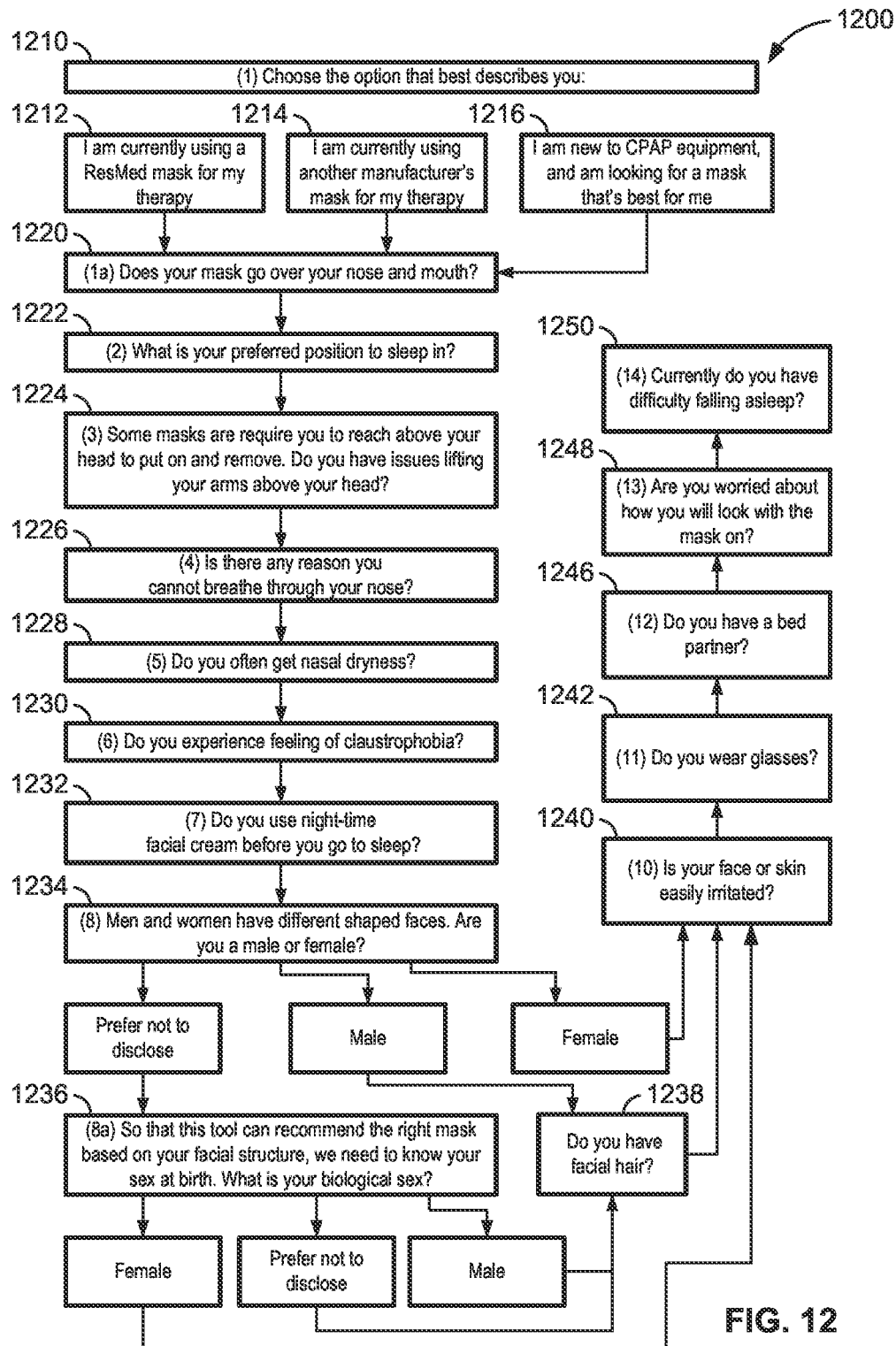
FIG. 12 is a tree diagram of the feedback data collected in relation to determining mask design.

FIG. 12 shows a tree diagram 1200 of the data that is collected through the example application 360 described herein. An input 1210 requests what option best describes the user. The input 1210 may include a vendor manufactured mask user 1212, a third party manufactured mask user 1214, and a user without a current mask 1216. In the case that the user identifies themselves as a vendor manufactured mask user or a third party manufactured mask user, an input 1220 determines whether the mask goes over the nose or the nose and mouth. The data collection then collects data relating to sleep position 1222. In the case that the user indicates that they do not currently use a mask, the routine directly collects data relating to sleep position 1222. An input 1224 collects data on whether the user has difficulty putting their arms above their head. An input 1226 determines whether the user has difficulty breathing through their nose. An input 1228 determines whether the user suffers from nasal dryness. An input 1230 determines whether the user experiences claustrophobia. An input 1232 determines whether the user uses facial cream at night.

An input 1234 determines the gender of the user since different genders have generally different facial features. The user may select male or female. If the user declines to answers, an input 1236 determines the user's gender at birth. The user may answer male, female or decline to answer. If the user answers male to either input 1234 or 1236, an input 1238 determines whether the user has facial hair. The routine then presents a set of gender common questions including an input 1240 relating to whether face or skin is easily irritated, an input 1242 whether the user wears glasses, an input 1244 whether the user has a bed partner, an input 1246 whether the user is worried about their appearance with a mask 1248, and an input 1250 whether the user has difficulty falling asleep. As explained above, the collected data may be used to recommend or select an appropriate mask for a user. The collected data may also be categorized and correlated with other user specific data to provide guidelines for new mask designs relating a particular patient subpopulation or the general patient population.

For example, patient input data may indicate a mask leak at a certain area such as the top side of the nose. The leak may be confirmed through operational data from the RPT device. This data may then be correlated with the facial data relating to the top side of the nose. Analysis may be conducted to change the dimensions of the mask by lengthening the edge of the mask that interfaces with the top side of the nose to minimize the leak. Another example may be where patient input data indicates discomfort with the mask on the top side of the nose. This data may then be correlated with the facial data relating to the top side of the nose. Analysis may be conducted to change the dimensions of the mask by shortening the edge of the mask that interfaces with the top side of the nose to minimize the discomfort. Of course, the data may also be provided to health care provider to recommend different size or types of masks to reduce discomfort or leaking. Alternatively, the data may be used to modify a mask initially selected by the patient to be individually tailored to the patient.

The collected patient data from the above application and additional data such as operational data from the RPT device 250 in FIG. 5 may be transforming or processed in a data processing step to assist in designing an improved interface for that user. A mirror image of a scanned face (superficial topography) may be used to create an interface such as a mask. Such a patient interface, however, is not necessarily ideal, because certain areas of the sealing region on the face may require different levels of sealing force, or are more sensitive to tight headgear pressure, or are more likely to have a leak in that location due to complex facial geometry. These finer details relevant to performance and comfort are accounted for with additional processing resulting in more optimal mask designs.

In one example, the relaxed state geometry data from relaxed state data collection may be used to try and provide an indication of the deformed state geometry if it cannot be directly measured or is unavailable. Simulation software may be used in relaxed data post processing to simulate the deformed state. Examples of suitable simulation software may include but is not limited to ANSYS which performs a transformation from 'relaxed' to 'deformed' state geometry data in relaxed data.

Additional facial image may be taken to determine relaxed and deformed states of facial geometry. With both the 'Relaxed' and 'Deformed' states of geometry data, Finite element software (such as ANSYS) may be used to calculate approximate pressure values experienced between the patient interface contact area and the face of a patient in simulating experienced pressure. Alternatively, pressure data may be gathered separately via pressure mapping. Thus, from relaxed state data collection, the deformed geometry may be estimated as well as the experienced pressure.

With the measured data, either geometric or pressure data, areas or features on the patient's face, which require special consideration may be determined and addressed in specific feature processing. Optionally, data from any combination of measurement sources may provide a comprehensive model that includes both the geometry and pressure data sets to further the goals of providing comfort, efficacy and compliance of the design.

The face is not a static surface. Rather it adapts and changes to interactions with external conditions, such as forces from a patient interface, air pressure on the face and gravity. By accounting for these interactions, additional benefits are gained in providing the optimum seal and comfort to the patient. Three examples illustrate this processing.

First, since the user wearing these patient interfaces will experience CPAP pressure, this knowledge may be used to enhance the comfort and sealing of the patient interface. Simulation software along with known characteristics (e.g. soft tissue properties or elastic moduli) may help predict the deformations the surfaces of the face will experience at a particular air pressure within the patient interface.

Tissue properties may be known and gathered for a population relating to any of the following facial locations: supraglabella, glabella, nasion, end of nasal, mid-philtrum, upper lip margin, lower lip margin, chin-lip fold, mental eminence, beneath chin, frontal eminence, supra orbital, lateral glabella, lateral nasal, suborbital, inferior malar, lateral nostril, naso-labial ridge, supra canina, sub canina, mental tubercle ant., mid lateral orbit, supraglenoid, zygomatic, lateral, supra-M2, mid-masseter muscle, occlusal line, sub-m2, gonion, and the mid mandibular angle.

For example, soft tissue thickness is known from anthropometric databases for at least one of the following facial features such as the nasian, the end of nasal, the mid-philtrum, the chin-lip fold, the mental eminence, the suborbital, the inferior malar, the lateral nostril, the naso-labial ridge, the supra canina, and the sub canina. Certain locations such as the suborbital, the inferior malar, the lateral nostril, the naso-labial ridge, the supra canina, and the sub canina are disposed on both sides of the face.

Known tissue properties at any one or more of these locations may include any one or more of soft tissue thickness, modulus data based on force, deflection, modulus and thickness, soft tissue thickness ratio information, and body mass index (BMI).

Second, the skin surfaces on a patient's face significantly deform when a CPAP patient interface is strapped onto a face. Using the initial 3D measurement of the geometric surfaces of the head and face in the relaxed state, the changes in the surfaces may be predicted using knowledge of the skin/soft tissue properties, discussed above, and simulation software. Such a technique may be an iterative, optimization process coupled with the design process.

Third, given a sleeping position, the skin surfaces may shift due to gravity. Predicting these changes, by using knowledge of skin and soft tissue properties along with simulation software, can help to design more robust comfortable and high performance patient interfaces in various sleeping positions. Data relating to upright to supine change in geometry may be collected and used from one or more facial areas of interest such as the nasian, the end of nasal, the mid-philtrum, the chin-lip fold, the suborbital, the lateral nostril, the naso-labial ridge, the supra canina, and the sub canina.

Finite Element Analysis (FEA) software (such as ANSYS) may be used to calculate an approximate pressure value experienced between the interface contact area and the user's face. In one form, inputs may include geometry of the face in the 'Relaxed' and 'Deformed' states, characteristics (e.g. measured elastic moduli, or sub-structures with known characteristics such as stiffnesses) of the face at various locations thereof. Using such inputs, a finite element (FE) model of the face may be constructed, which could then be used to predict one or more responses of the face to an input (such as deformation or load). For example, the FE model of the face could be used to predict the deformed shape of the face for a given pressure level in the patient interface (e.g. 15 cmH2O). In some forms, the FE model may further include a model of the patient interface or a portion thereof, such as a cushion, comprising a geometry of the cushion and its characteristics (e.g. mechanical properties such as elastic modulus). Such a model could predict a deformation of the cushion when an internal load is applied thereto, such as from an application of CPAP pressure, and a resulting interaction of the cushion with the face, including the loads/pressures therebetween, and a deformation of the face. Specifically, the change in distance at each point between the relaxed state and the deformed state along with the corresponding tissue properties may be used to predict the pressure experienced at a given point (e.g., at a cheekbone).

Certain areas or features on a face may require special consideration. Identifying and adjusting for these features may improve the overall comfort of the interface. From the data collection and estimation techniques discussed above, suitable features may be applied to a custom patient interface.

In addition to the pressure sensitivity, pressure compliance, shear sensitivity and shear compliance indicators above, special considerations may be accorded to facial hair, hair styles, and extreme facial landmarks, such as a pronounced nose bridge, sunken cheeks or the like. As used herein, "shear sensitivity" refers to the feeling of shear by the patient, while "shear compliance" refers to how willing the patient's skin is to move along or compliant with shear.

Figure 13:
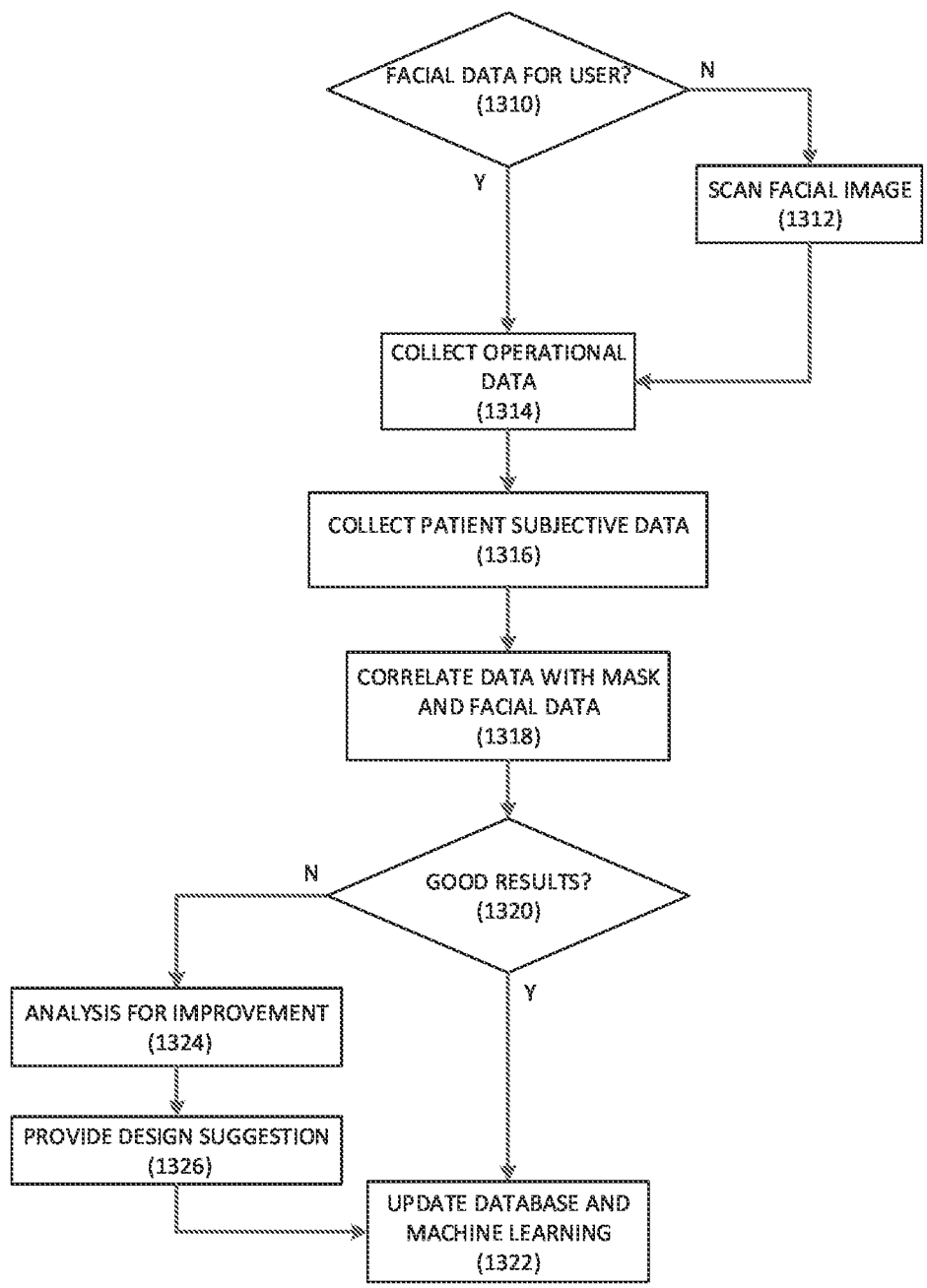
FIG. 13 is a flow diagram of the process of collection of feedback data from a patient for determining mask characteristics.

FIG. 13 is a feedback data collection routine that may be run a specific time period or time periods after the initial selection of the interface by a patient. For example, the follow up routine may be run over the first two days of the use of an interface with the RPT. The flow diagram in FIG. 13 is representative of example machine readable instructions for collecting and analyzing feedback data to select characteristics of an interface for respiratory pressure therapy that are optimized for different patient types. In this example, the machine readable instructions comprise an algorithm for execution by: (a) a processor; (b) a controller; and/or (c) one or more other suitable processing device(s). The algorithm may be embodied in software stored on tangible media such as flash memory, CD-ROM, floppy disk, hard drive, digital video (versatile) disk (DVD), or other memory devices. However, persons of ordinary skill in the art will readily appreciate that the entire algorithm and/or parts thereof can alternatively be executed by a device other than a processor and/or embodied in firmware or dedicated hardware in a well-known manner (e.g., it may be implemented by an application specific integrated circuit [ASIC], a programmable logic device [PLD], a field programmable logic device [FPLD], a field programmable gate array [FPGA], discrete logic, etc.). For example, any or all of the components of the interfaces can be implemented by software, hardware, and/or firmware. Also, some or all of the machine readable instructions represented by the flowcharts may be implemented manually. Further, although the example algorithms are described with reference to the flowchart illustrated in FIG. 13, persons of ordinary skill in the art will readily appreciate that many other methods of implementing the example machine readable instructions may alternatively be used. For example, the order of execution of the blocks may be changed, and/or some of the blocks described may be changed, eliminated, or combined.

As will be explained below, the routine in FIG. 13 may provide a recommendation for design modifications on different characteristics of the interface such as the areas in contact with the facial area. This data may also continuously update the example machine learning driven correlation engine.

The routine first determines whether facial data has already been collected for the patient (1310). If facial data has not been collected, the routine activates the application 360 to request a scan of the face of the user using a mobile device running the above described application such as the mobile device 234 in FIG. 5 (1312).

After the facial image data is collected (1312) or if the facial data already is stored from a previous scan, the routine then accesses collected operational data from the RPT over a set period such as 2 days of use (1314). Of course other appropriate periods greater than or less than two days may be used as a time period to collect operational data from the RPT and other relevant data. For example, the system in FIG. 2 may collect complied objective data from two days of use such as time of use or leak data from the RPT 250.

In addition, subjective feedback data such as seal, comfort, general likes/dislikes etc., may be collected from an interface of the user application 360 executed by the computing device 230 (1316). As explained above, the subjective data may be collected via interfaces that provide questions to the patient. The subjective data may thus include answers relating to discomfort or leaks and psychological safety questions, such as whether the patient is psychologically comfortable with the mask. Other data may be collected based on visual displays of the mask in relation to an image of the face.

The routine then correlates objective data and subjective data along with the selected mask type and the facial scan data of the patient (1318). In the case of a good result, the routine will determine that the operational data shows high compliance, low leak, and a good subjective result data from the patient (1320). The routine then updates the database and learning algorithm as a successful mask characteristics or features with the correlated data (1322). If the case is not a good result, the routine also analyzes the correlated data and determines whether the results may be improved by adjusting the characteristics of the mask (1324). The routine then suggests alterations to the characteristics in accordance with the analysis (1326). For example, the routine may suggest that the part of the mask that joins the nose be thickened to prevent a detected or reported leak. The routine then stores the results by updating the database and learning algorithm (1322).

Figure 14:
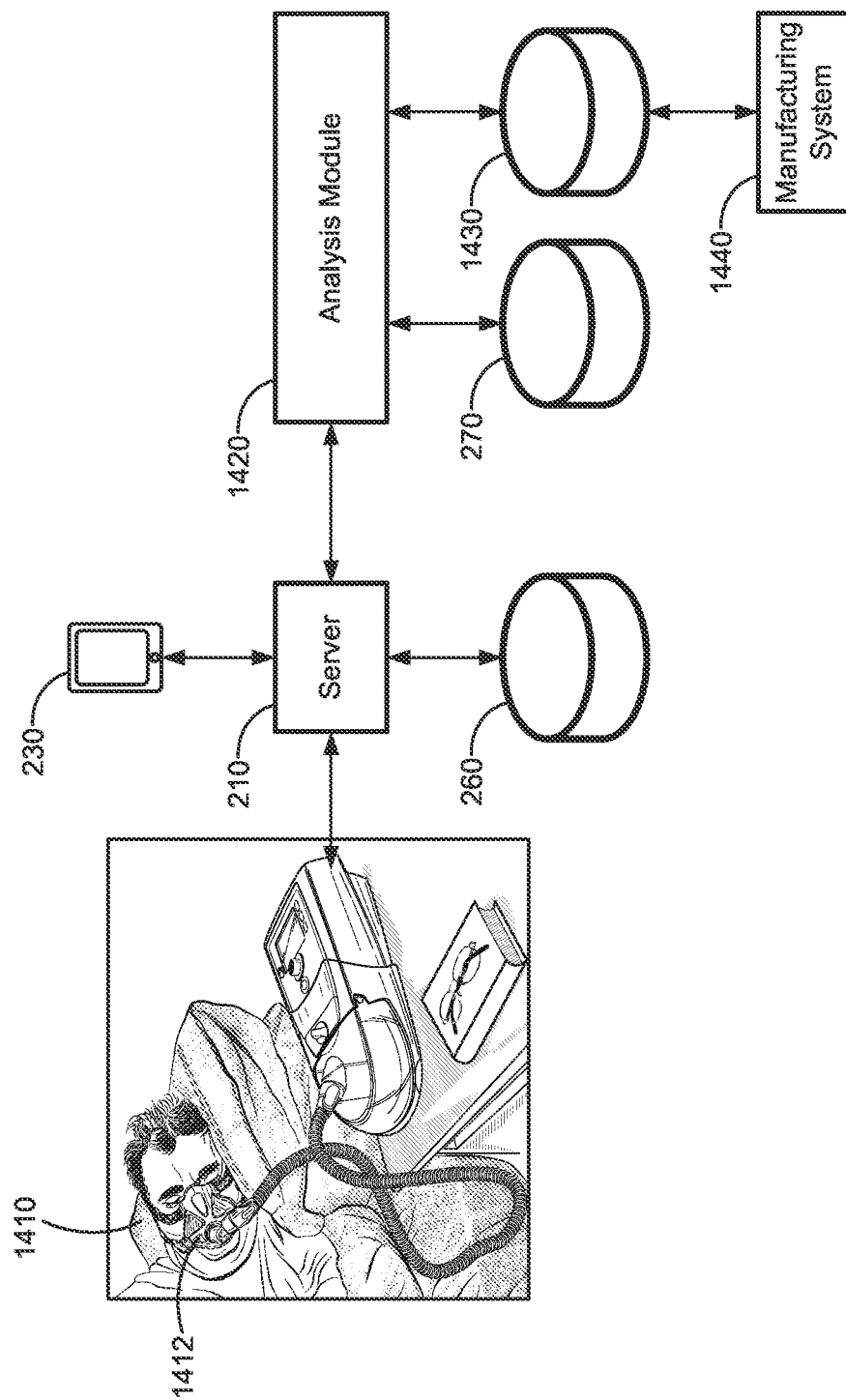
FIG. 14 is a diagram of a system to produce modified interfaces based on collected feedback data.

FIG. 14 is an example production system 1400 that produces modified interfaces based on the collected data from the data collection system 200 in FIG. 5. The server 210 provides collected operational data from a population of RPT devices 1410, and subjective data gathered by the application 360 from a population of patients 1412 to an analysis module 1420.

The analysis module 1420 includes access to the interface database 270 that includes data relating to different models of masks for one or more different manufacturers. The analysis module 1420 may include a machine learning routine to provide suggested changes to characteristics or features of an interface for a specific patient or an interface used by one subgroup of the population of patients. For example, the collected operation and patient input data in conjunction with facial image data may be input to the analysis module 1420 to provide anew characteristic for the mask design. The manufacturing data such as CAD/CAM files for existing mask designs are stored in a database 1430. The modified design is produced by the analysis module and communicated to a manufacturing system 1440 to produce a mask with the modifications in dimensions, sizing, materials, etc. In this example, the manufacturing system 1440 may include tooling machines, molding machines, 3D printing systems, and the like to produce masks.

For a more efficient method of manufacturing custom components than additive manufacturing, the molding tools in the manufacturing system 1440 can be rapidly prototyped (e.g., 3D printed) based on the proposed modifications. In some examples, rapid three-dimensional printed tooling may provide a cost-effective method of manufacturing low volumes. Soft tools of aluminum and/or thermoplastics are also possible. Soft tools provide a low number of molded parts and are cost effective compared to steel tools.

Hard tooling may also be used during the manufacture of custom components. Hard tooling may be desirable in the event of favorable volumes of interfaces being produced based on the collected feedback data. Hard tools may be made of various grades of steel or other materials for use during molding/machining processes. The manufacturing process may also include the use of any combination of rapid prototypes, soft and hard tools to make any of the components of the patient interface. The construction of the tools may also differ within the tool itself, making use of any or all of the types of tooling for example: one half of the tool, which may define more generic features of the part may be made from hard tooling, while the half of the tool defining custom components may be constructed from rapid prototype or soft tooling. Combinations of hard or soft tooling are also possible.

Other manufacturing techniques may also include multi-shot injection molding for interfaces having different materials within the same component. For example, a patient interface cushion may include different materials or softness grades of materials at different areas of the patient interface. Thermoforming (e.g., vacuum forming), which involves heating sheets of plastic and vacuuming the sheets onto the tool mold and then cooling the sheets until it takes the shape of the mold may also be used. This is a viable option for molding components of the custom nare cover. In a yet another form, a material which may be initially malleable may be used to produce a customized patient interface frame (or any other suitable component such as a headgear or portions thereof, such as a rigidizer). A 'male' mold of the patient may be produced using one or more techniques described herewithin, upon which a malleable 'template' component may be placed to shape the component to suit the patient. Then, the customized component may be 'cured' to set the component so that it would no longer be in a malleable state. One example of such a material may be a thermosetting polymer, which is initially malleable until it reaches a particular temperature (after which it is irreversibly cured), or a thermosoftening plastic (also referred to as thermoplastic), which becomes malleable above a particular temperature. Custom fabric weaving/knitting/forming may also be used. This technique is similar to three-dimensional printing processes except with yarn instead of plastic. The structure of the textile component may be knitted into any three-dimensional shapes, which are ideal for fabricating custom headgear.

As used in this application, the terms "component," "module," "system," or the like, generally refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller, as well as the controller, can be a component. One or more components may reside within a process and/or thread of execution, and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

One or more elements or aspects or steps, or any portion(s) thereof, from one or more of any of the claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations or alternative implementations according to aspects of the present disclosure may combine any number of features from any of the implementations described herein, such as, for example, in the alternative implementations described below.

What is claimed is:

1. A mobile device comprising:
    a camera;
    a display;
    a computer readable medium storing application instructions; and
    a controller coupled to the camera, the display, and the computer readable medium, the controller operable to execute the application instructions to cause the controller to:
        capture a facial image of a user via the camera, wherein the user wears an interface for a respiratory therapy device when the user uses the respiratory therapy device;
        overlay a location grid in the shape of the interface for the respiratory therapy device over a facial image on the display, the location grid including a plurality of areas each defined by lines in the grid representing contact between the interface for the respiratory therapy device and the face of the user;
        provide a graphical indicator for accepting a user selection in at least one of the plurality of areas of the grid as to discomfort for contact or to a leak in the interface; and
        generate an input interface on the display to collect user input data from the user relating to the interface for the respiratory therapy device, wherein user input data relating to the interface and the facial image data is stored in the computer readable medium.

2. The mobile device of claim 1, wherein the interface for the respiratory therapy device is a mask.

3. The mobile device of claim 1, wherein the respiratory pressure therapy device is one of a Continuous Positive Airway Pressure (CPAP) device, a Non-invasive ventilation (NIV) device, or an invasive ventilation device.

4. The mobile device of claim 1, further comprising a transceiver to send the stored facial data and user input data to an external system.

5. The mobile device of claim 4, wherein the external system receives the facial image data and the user input and sends an appropriate interface size to the mobile device for display to the user.

6. The mobile device of claim 1, further comprising an audio speaker, wherein the application instructions cause audio instructions to be played for the user for capturing the facial image data and providing the user input data.

7. The mobile device of claim 1, wherein the application instructions cause an instructional video to be played on the display for the user for capturing the facial image data.

8. The mobile device of claim 1, wherein the application instructions cause the controller to generate an input interface on the display for requesting information relating to the interface for the respiratory therapy device currently worn by the user.

9. The mobile device of claim 1, wherein the application instructions cause the controller to generate an input interface on the display to provide user specific demographic information.

10. The mobile device of claim 1, wherein the application instructions cause the controller to generate an input interface on the display to allow the user to enter subjective data via a questionnaire with questions relating to the comfort of the interface for the respiratory therapy device worn by the user.

11. The mobile device of claim 1, wherein the application instructions cause the controller to generate an input interface on the display to allow the user to enter data relating to sleep by the user when wearing the interface for the respiratory therapy device.

12. The mobile device of claim 1, wherein the application instructions cause the controller to display graphics on the display showing different interfaces for the respiratory therapy device for selection by the user on the display.

13. A non-transitory computer readable medium having stored thereon instructions that, when executed by a processor unit, cause the processor unit to:
    capture a facial image of a user via a camera, wherein the user wears an interface for a respiratory therapy device when the user uses the respiratory therapy device;
    overlay a location grid in the shape of the interface for the respiratory therapy device over a facial image on the display and wherein the location grid includes a plurality of areas each defined by lines in the grid representing contact between the interface for the respiratory therapy device and the face of the user;
    provide a graphical indicator for accepting a user selection in at least one of the plurality of areas of the grid as to discomfort for contact or to a leak in the interface;
    generate an input interface on a display to collect user input data from the user relating to the interface for the respiratory therapy device; and
    store user input data relating to the interface and the facial image data in the computer readable medium.

14. A system to collect feedback data from a user who wears an interface with a respiratory pressure therapy device, the system comprising:
    storing application instructions on a non-transitory computer readable medium;
    a data communication interface coupled to the non-transitory computer readable medium, the data communication interface in communication with a mobile device, the data communication interface allowing transmission of the application instructions to the mobile device, wherein the application instructions cause a controller of the mobile device to:
        capture a facial image of a user via the camera, wherein the user wears an interface for a respiratory therapy device when the user uses the respiratory therapy device;

generate an input interface on the display to collect user input data from the user relating to the interface for the respiratory therapy device;

overlay a location grid in the shape of the interface for the respiratory therapy device over a facial image on the display and wherein the location grid includes a plurality of areas each defined by lines in the grid representing contact between the interface for the respiratory therapy device and the face of the user;

provide a graphical indicator for accepting a user selection in at least one of the plurality of areas of the grid as to discomfort for contact or to a leak in the interface; and store user input data relating to the interface and the facial image data in a storage device.

15. The system of claim 14, wherein the interface is a mask and wherein the respiratory pressure therapy device is one of a Continuous Positive Airway Pressure (CPAP) device, a Non-invasive ventilation (NIV) device, or an invasive ventilation device.

16. The system of claim 14, wherein the instructions cause the controller to control a transceiver to send the stored facial data and user input data to the data communication interface.

17. The system of claim 14, wherein the application instructions cause the controller to:

generate an interface on the display for requesting information relating to the interface for the respiratory therapy device currently worn by the user;

generate an input interface on the display to provide user specific demographic information;

generate an input interface on the display to allow the user to enter subjective data via a questionnaire with questions relating to the comfort of the interface for the respiratory therapy device worn by the user; and generate an input interface on the display to allow the user to enter data relating to sleep by the user when wearing the interface for the respiratory therapy device.

18. The system of claim 14, wherein the interface for the respiratory therapy device is a mask.

19. The system of claim 14, wherein the application instructions cause audio instructions to be played on an audio speaker for the user for capturing the facial image data and providing the user input data, or wherein the application instructions cause an instructional video to be played on the display for the user for capturing the facial image data.

20. The system of claim 14, wherein the application instructions cause the controller to display graphics on the display showing different interfaces for the respiratory therapy device for selection by the user on the display.

* * * * *